United States Patent [19]
Lal et al.

[11] Patent Number: 5,728,089
[45] Date of Patent: Mar. 17, 1998

[54] MICROFABRICATED STRUCTURE TO BE USED IN SURGERY

[75] Inventors: Amit Lal; Richard M. White, both of Berkeley, Calif.

[73] Assignee: The Regents of the University of California, Oakland, Calif.

[21] Appl. No.: 332,543

[22] Filed: Oct. 31, 1994

Related U.S. Application Data

[63] Continuation-in-part of Ser. No. 306,843, Sep. 14, 1994, Pat. No. 5,569,968, which is a continuation of Ser. No. 72,294, Jun. 4, 1993, abandoned.

[51] Int. Cl.$^6$ .................................................. A61B 17/32
[52] U.S. Cl. .................................. 606/1; 606/169; 601/2; 604/22
[58] Field of Search ........................ 606/1, 38, 39, 606/41, 42, 45–48, 107, 167, 169–171; 601/2; 604/22; 128/662.05, 662.06, 662.03; 310/311, 321, 322, 334

[56] References Cited

U.S. PATENT DOCUMENTS

| | | | |
|---|---|---|---|
| 3,952,732 | 4/1976 | Shock | 606/128 |
| 4,425,115 | 1/1984 | Wuchinich | 604/22 |
| 4,428,748 | 1/1984 | Peyman et al. | 604/22 |
| 4,634,420 | 1/1987 | Spinosa et al. | 604/22 |
| 4,764,244 | 8/1988 | Chitty et al. | |
| 4,783,821 | 11/1988 | Zdeblick et al. | |
| 4,802,476 | 2/1989 | Noerenberg et al. | 604/22 |
| 4,850,353 | 7/1989 | Stasz et al. | 606/39 |
| 4,936,281 | 6/1990 | Stasz | 606/50 |
| 4,980,021 | 12/1990 | Kitamura et al. | 606/167 |
| 5,006,749 | 4/1991 | White | |
| 5,025,346 | 6/1991 | Tang | |
| 5,026,387 | 6/1991 | Thomas | 606/169 |
| 5,049,775 | 9/1991 | Smits | 310/328 |
| 5,129,262 | 7/1992 | White et al. | |
| 5,162,691 | 11/1992 | Mariani et al. | |
| 5,189,914 | 3/1993 | White et al. | |
| 5,195,374 | 3/1993 | Parsons et al. | |
| 5,248,912 | 9/1993 | Muller et al. | |
| 5,295,487 | 3/1994 | Saitoh et al. | 128/662.03 |
| 5,336,062 | 8/1994 | Richter | |
| 5,339,289 | 8/1994 | Erickson | |
| 5,344,117 | 9/1994 | Trah et al. | |

OTHER PUBLICATIONS

Katyl, R. H., IBM Technical Disclosure Bulletin, "Monolithic Ultrasound Array", vol. 20, No. 6 Nov. 1977.
IBM Technical Disclosure Bulletin — Monolithic Ultrasound Array, vol. 20 No. 6, Nov. 1977 by R.H. Katyl.
Kim, E.S. et al., "Improved ICI–compatible piezoelectric Microphone and CMOS process," *Transducers*, 1991, San Francisco.
Kim, E.S. et al., "IC–processed Piezoelectric Microphone," *IEEE Electron Device Lett.*, vol. EDL–8, Oct. 1987, pp. 467–468.
Donk, et al., "Preliminary results of a silicon condenser microphone with internal feedback," *Transducers*, 1991 San Francisco.
Bearden, et al., *Optics Lett.*, vol. 18, No. 3, Feb. —93 pp. 238–240.
E. Graf, et al., "Silicon membrane condenser microphone with intergrated field–effect transistor, ".
*Sensors and Actuators A*, vol. 37–38 (Jun.–Aug.1993), pp. 708–711.
Junger, et al., *Sound Structures and Their Interaction*, pp. 235–272, MIT Press, 1986.

*Primary Examiner*—Jennifer Bahr
*Assistant Examiner*—Michael Peffley
*Attorney, Agent, or Firm*—Fish & Richardson, P.C.

[57] ABSTRACT

A microstructure suitable for use as a surgical instrument. The microstructure includes a silicon substrate having body and horn portions. The horn portion may include a blade with a forward edge. A piezoelectric actuator may be mechanically coupled to the body portion.

3 Claims, 23 Drawing Sheets

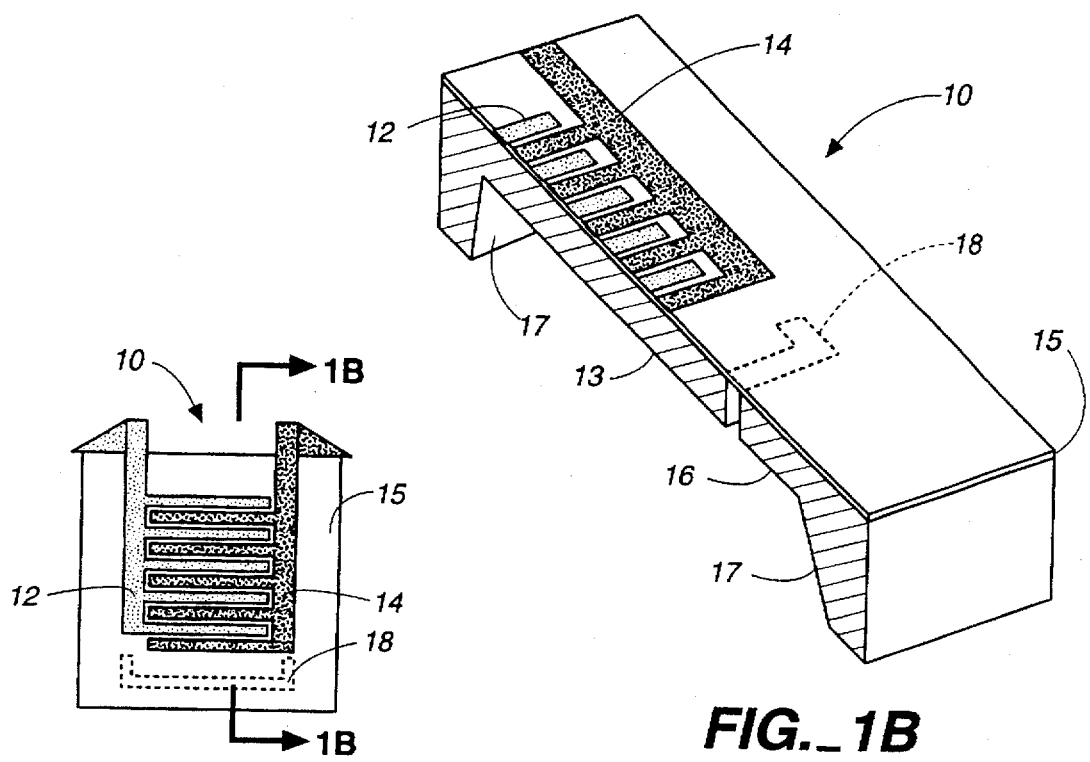
FIG._1A
FIG._1B
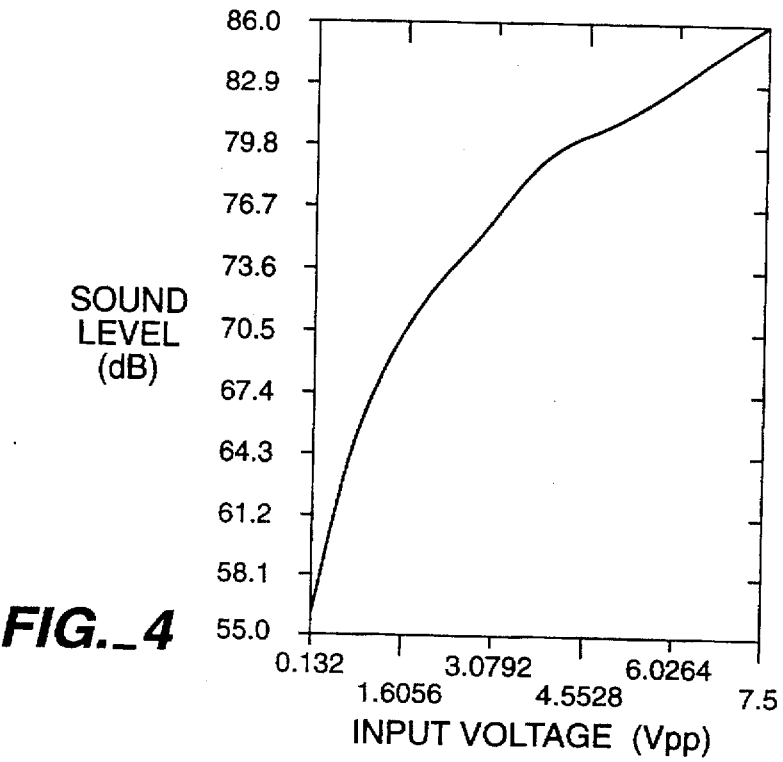
FIG._4

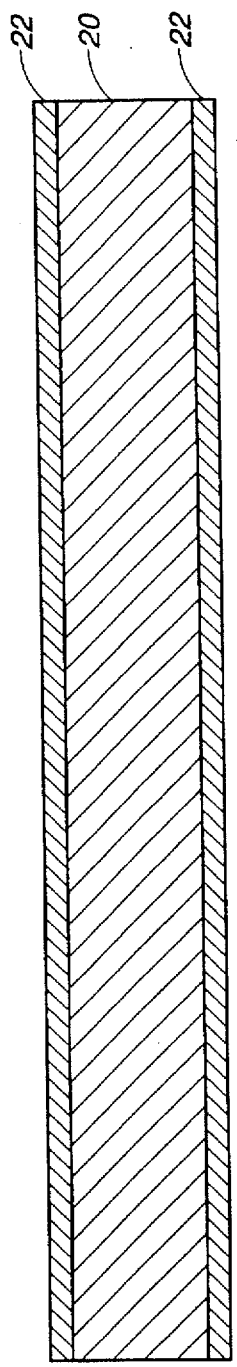
FIG._2A
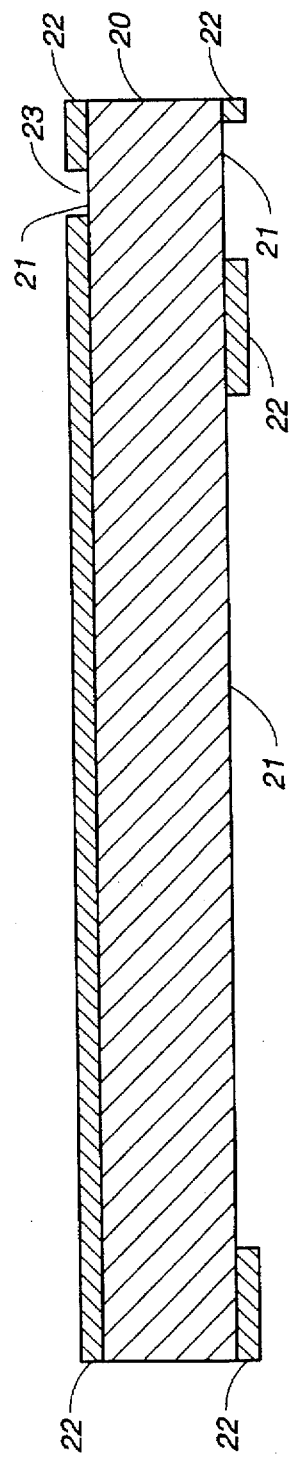
FIG._2B
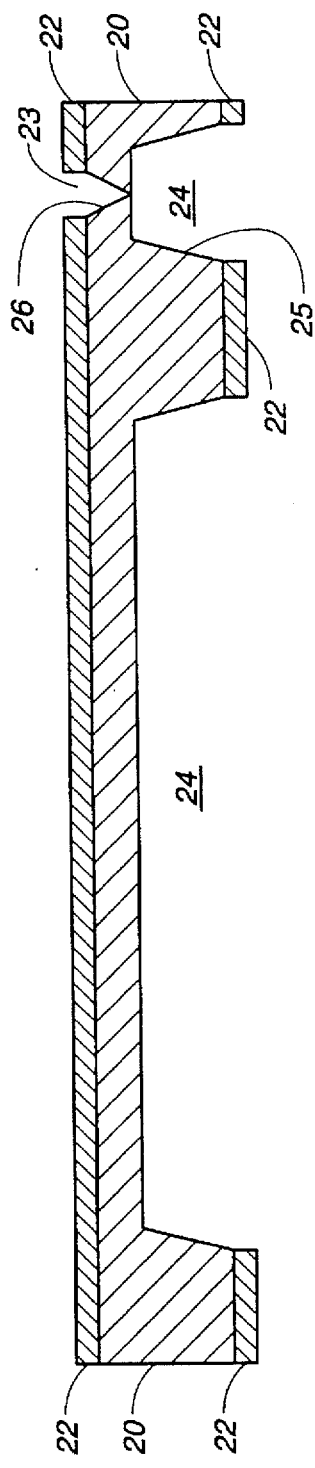
FIG._2C

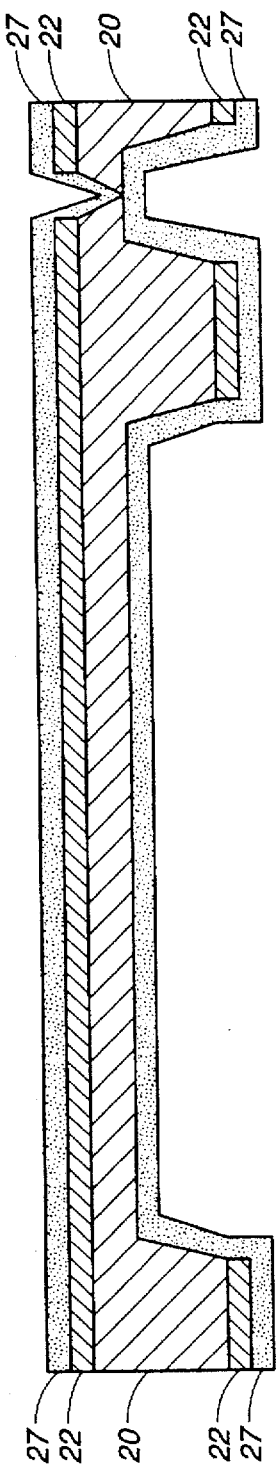
FIG._2D
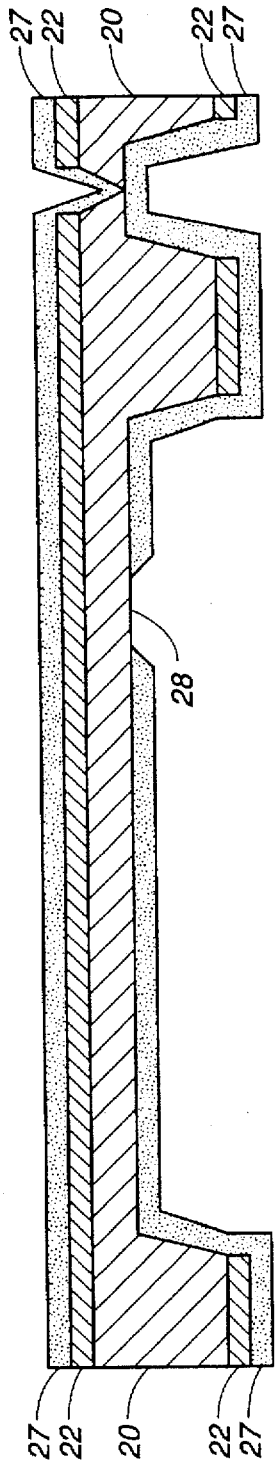
FIG._2E
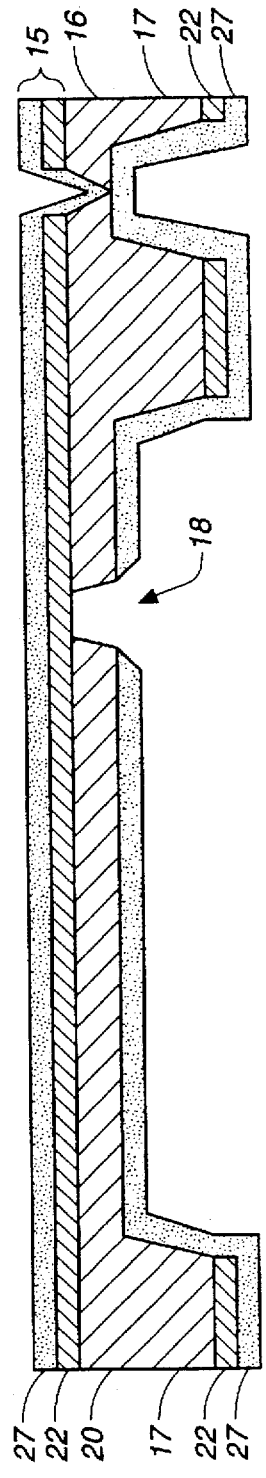
FIG._2F

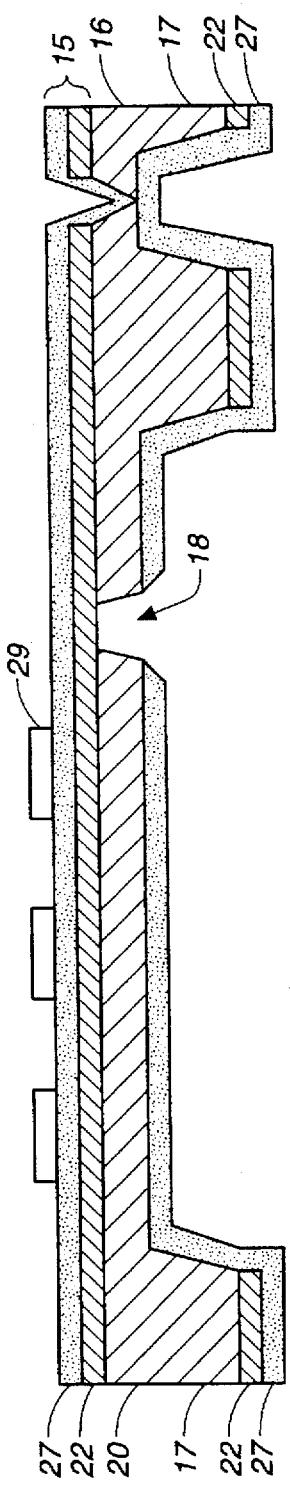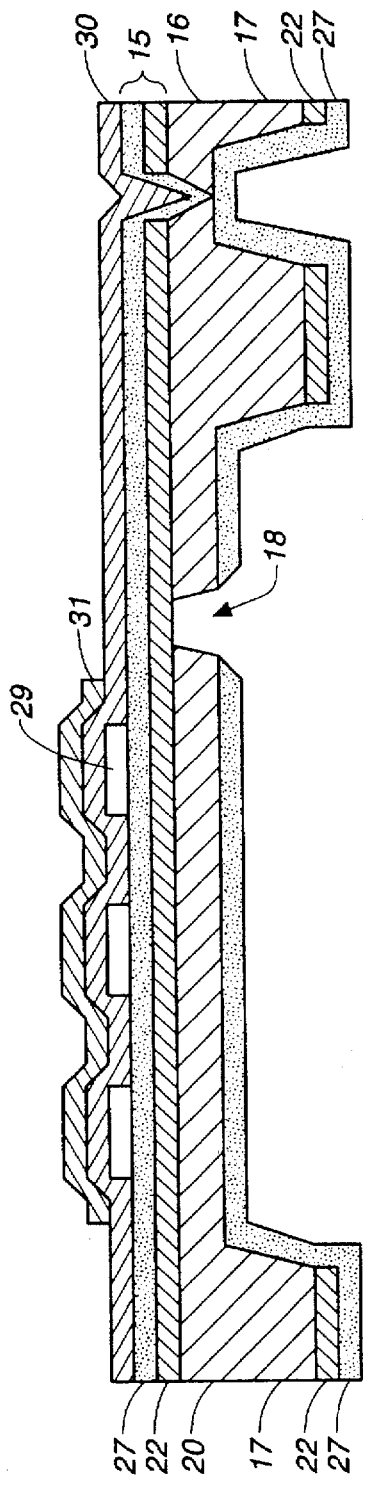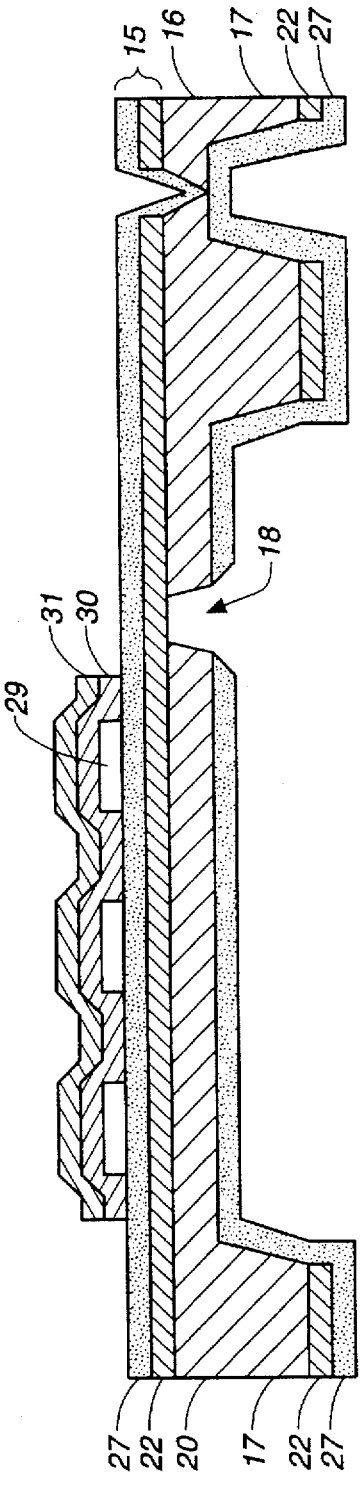

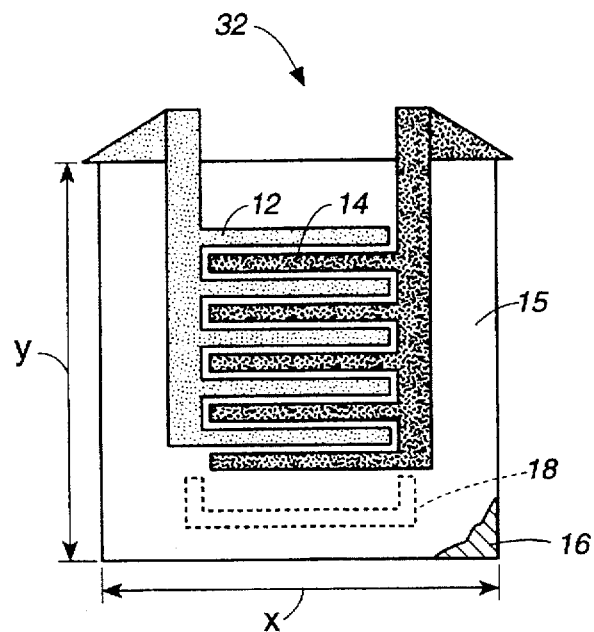
FIG._3A
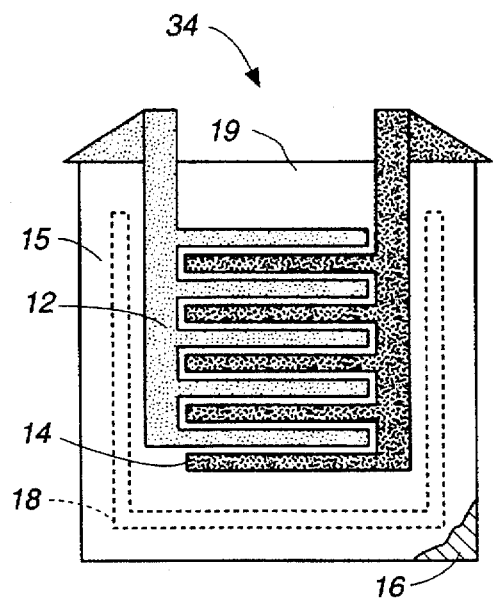
FIG._3B
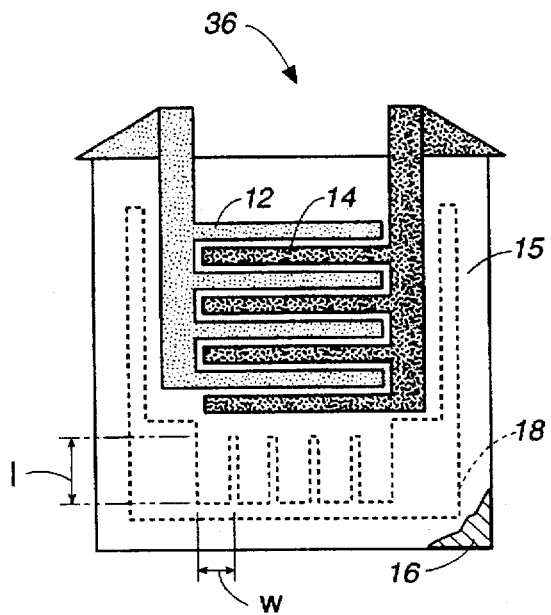
FIG._3C
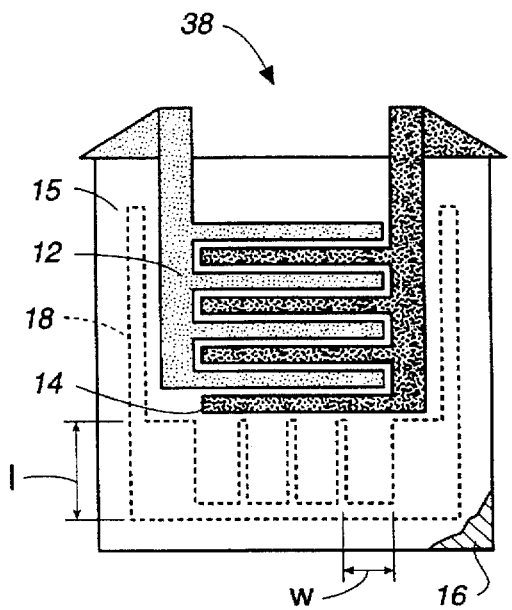
FIG._3D

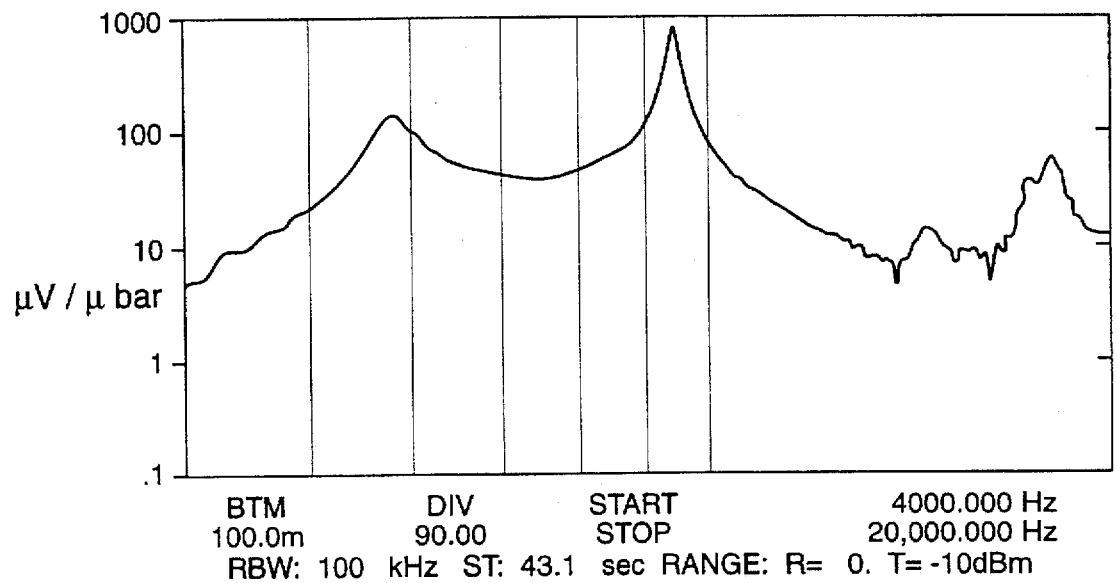
FIG._5A
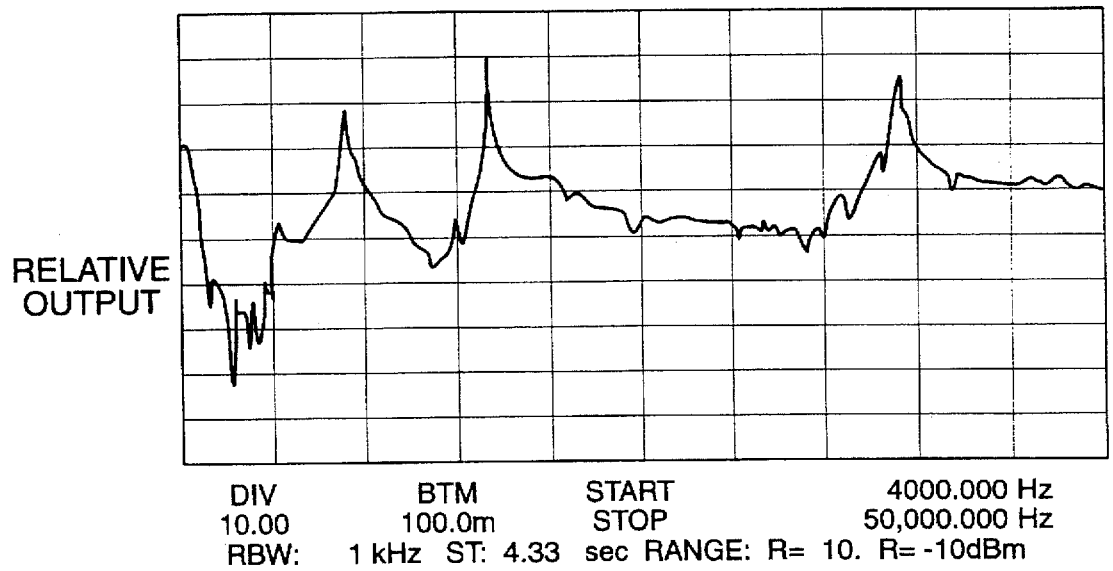
FIG._5B

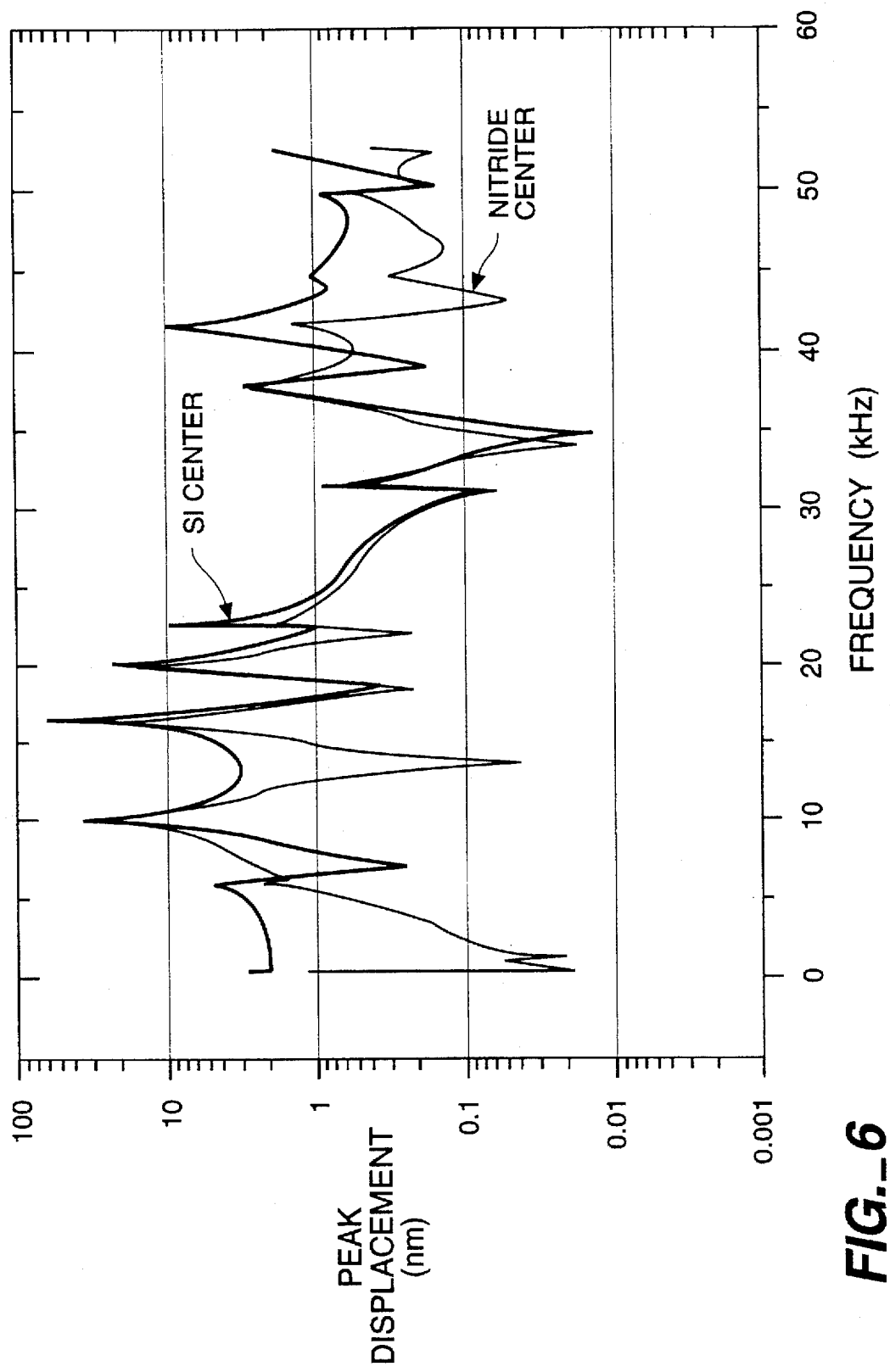
FIG._6

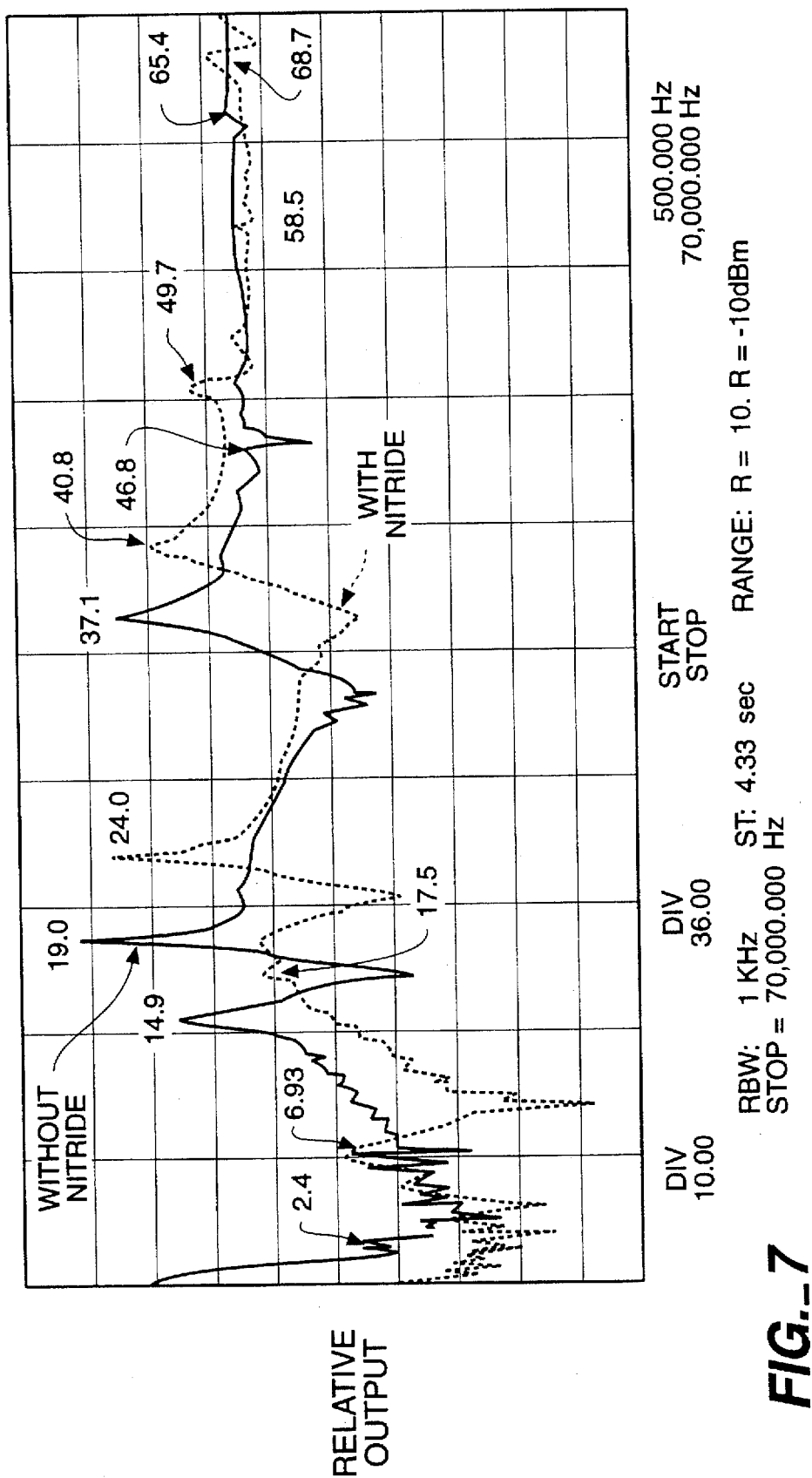
FIG._7

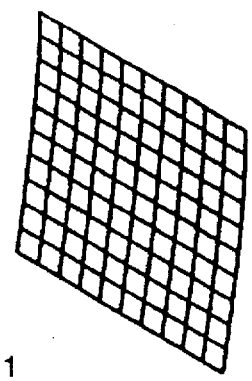
MODE 1
Frequency = 2059.8
Air wavelength = 16cm
FIG._8A
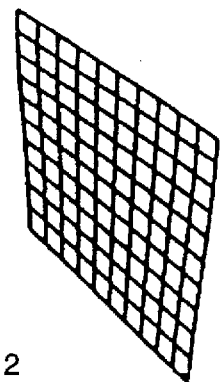
MODE 2
Frequency = 4876
Air wavelength = 6.77cm
FIG._8B
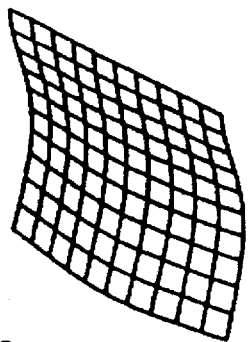
MODE 3
Frequency = 12562
Air wavelength = 2.63cm
FIG._8C
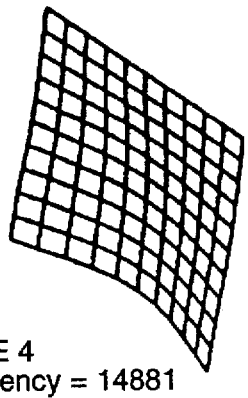
MODE 4
Frequency = 14881
Air wavelength = 2.21cm
Measured mode frequency > 14.9kHz
FIG._8D
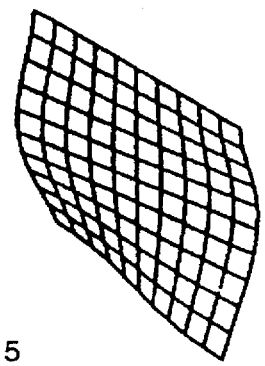
MODE 5
Frequency = 17935
Air wavelength = 1.84cm
Measured mode frequency > 19.0kHz
FIG._8E
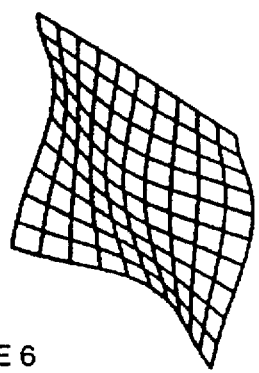
MODE 6
Frequency = 30607
Air wavelength = 1.08cm
FIG._8F

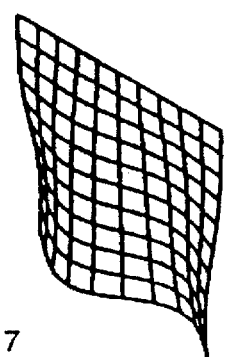
MODE 7
Frequency = 34549
Air wavelength = 0.95cm
FIG._8G
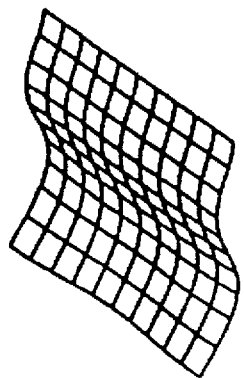
MODE 8
Frequency = 36367
Air wavelength = 0.91cm
Measured mode frequency > 37.1kHz
FIG._8H
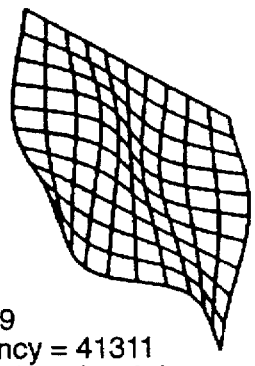
MODE 9
Frequency = 41311
Air wavelength = 0.8cm
FIG._8I
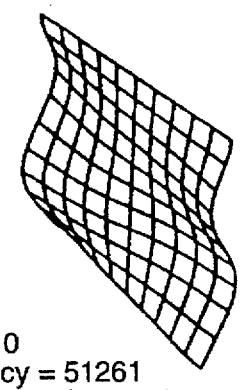
MODE 10
Frequency = 51261
Air wavelength = 0.64cm
FIG._8J
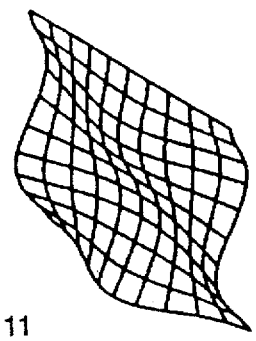
MODE 11
Frequency = 55360
Air wavelength = 0.596cm
FIG._8K
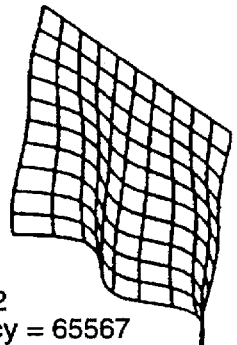
MODE 12
Frequency = 65567
Air wavelength = 0.5cm
Measured mode frequency > 65.4kHz
FIG._8L

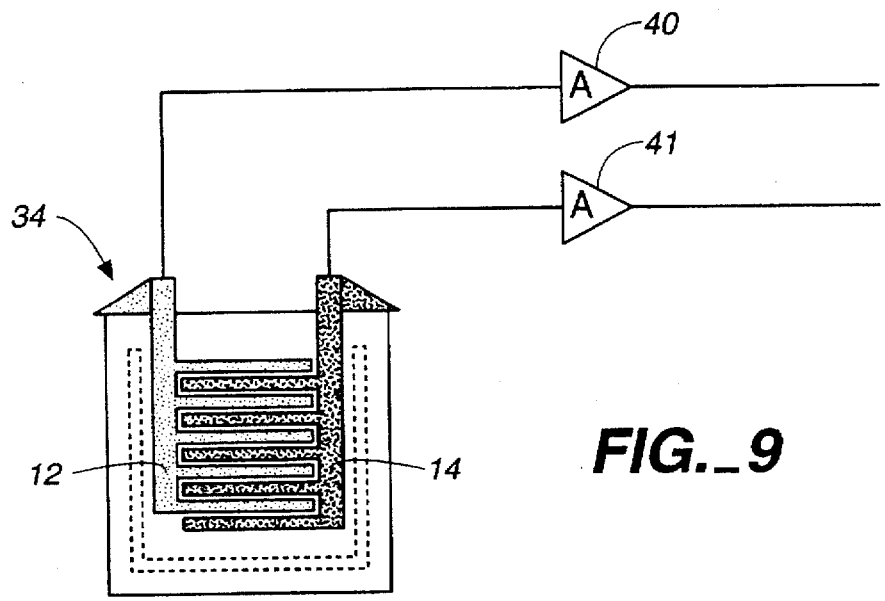
FIG._9
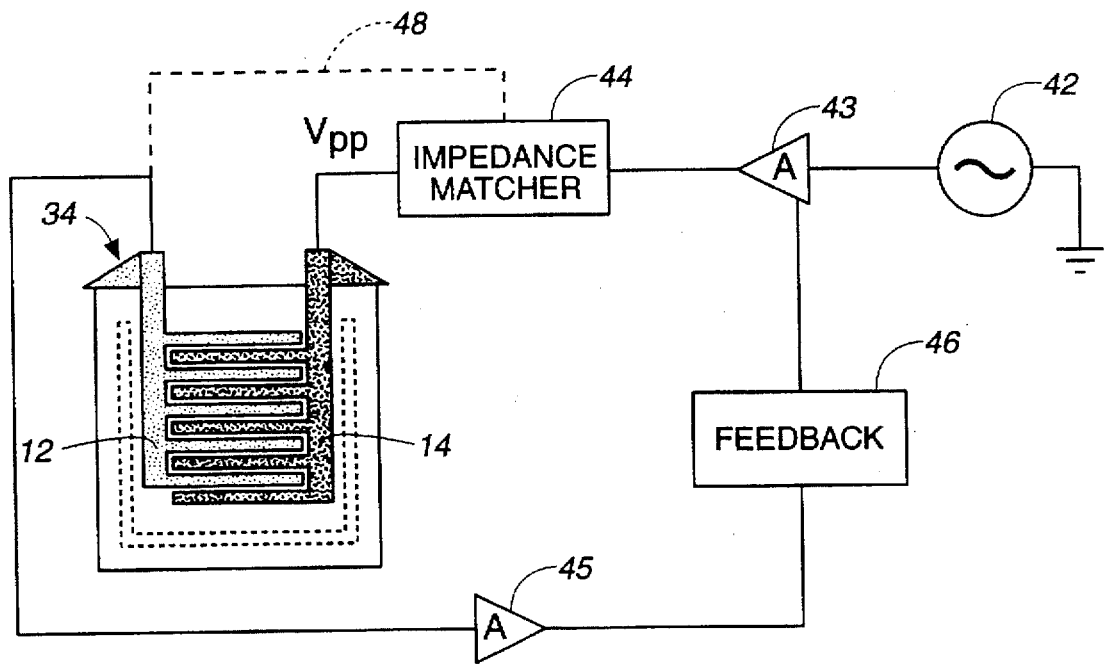
FIG._10

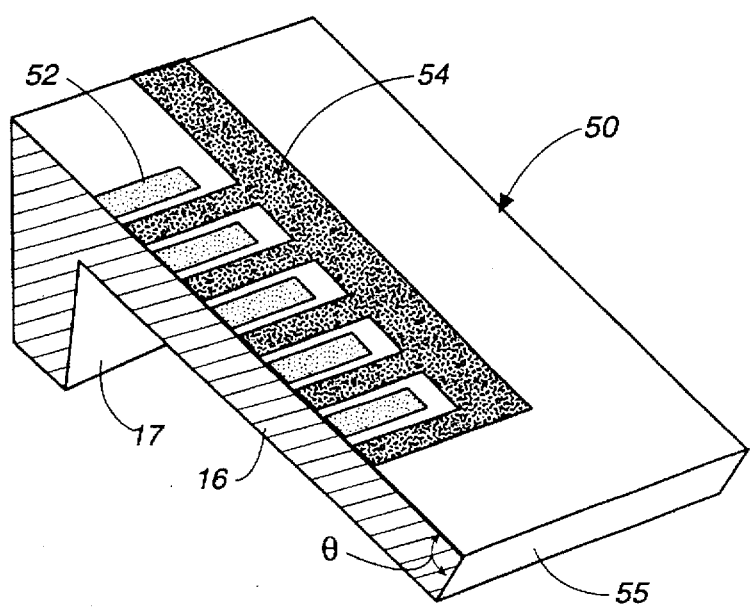
FIG._11A
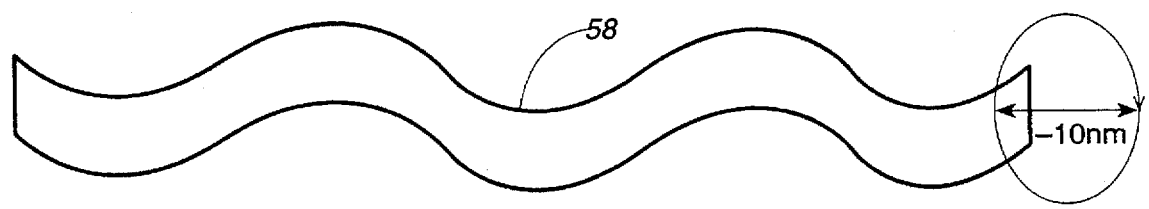
FIG._11B
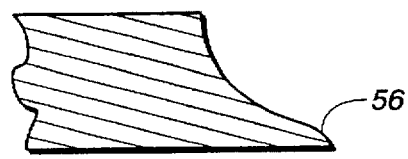
FIG._11C

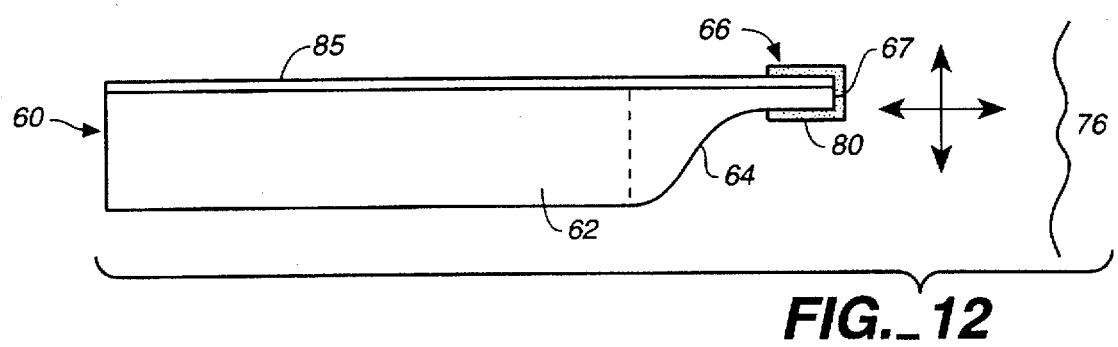
FIG._12
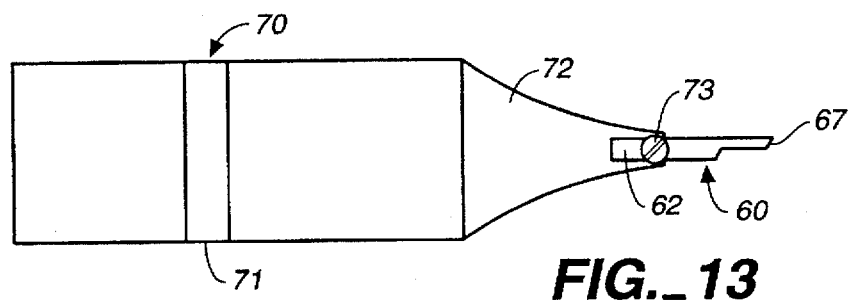
FIG._13
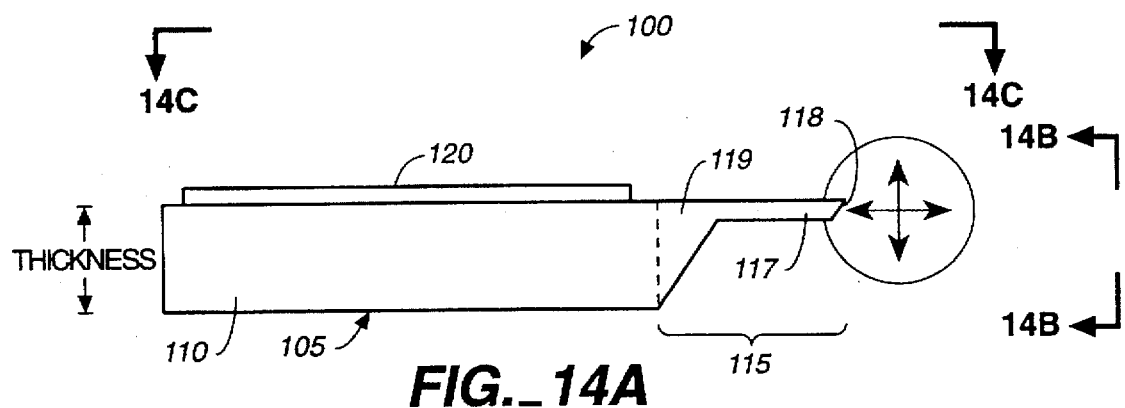
FIG._14A
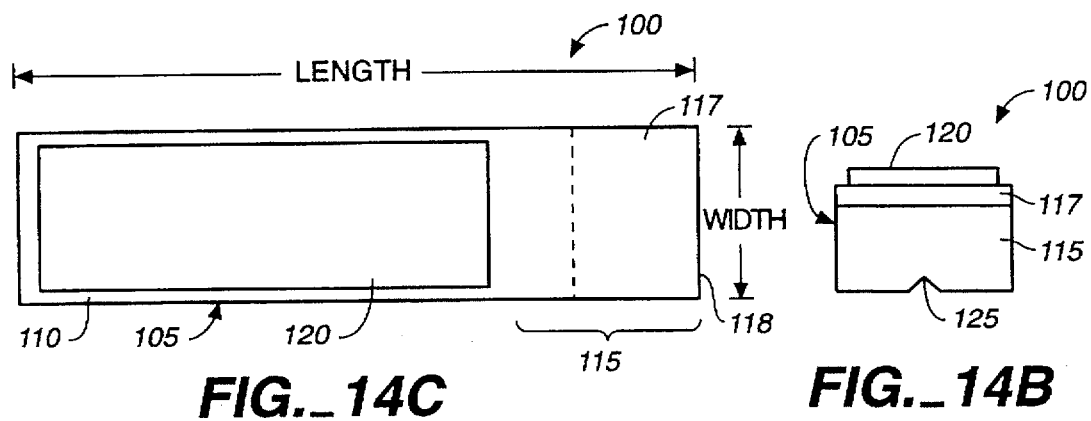
FIG._14C  FIG._14B

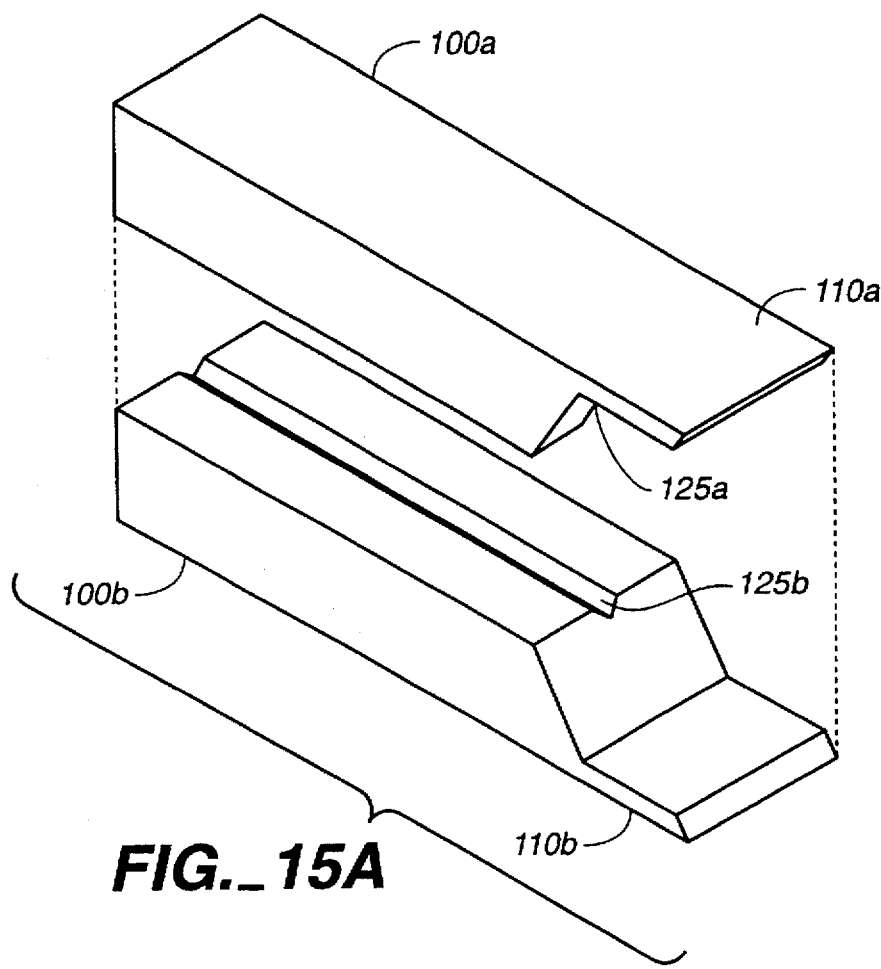
FIG._15A
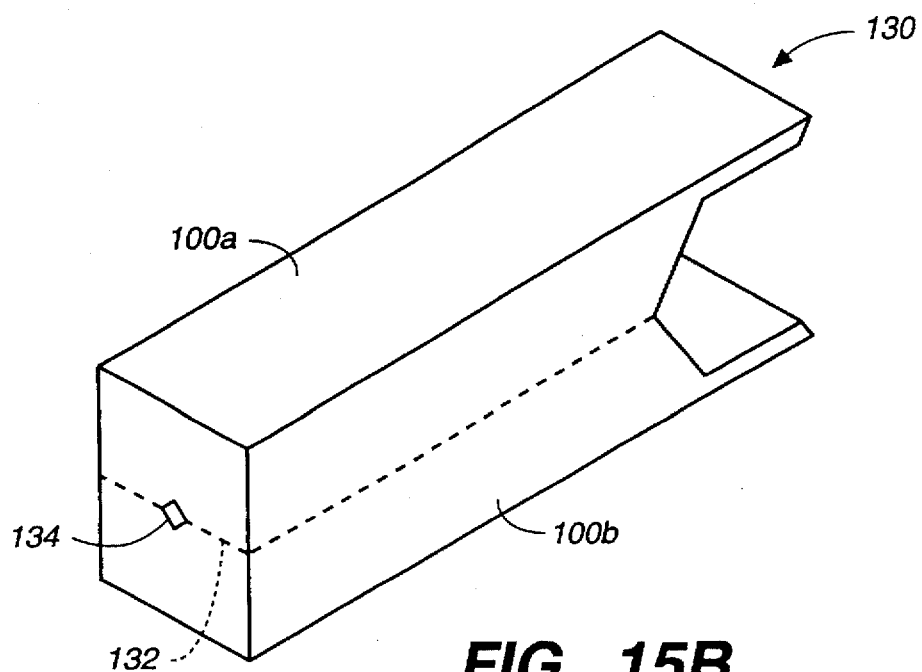
FIG._15B

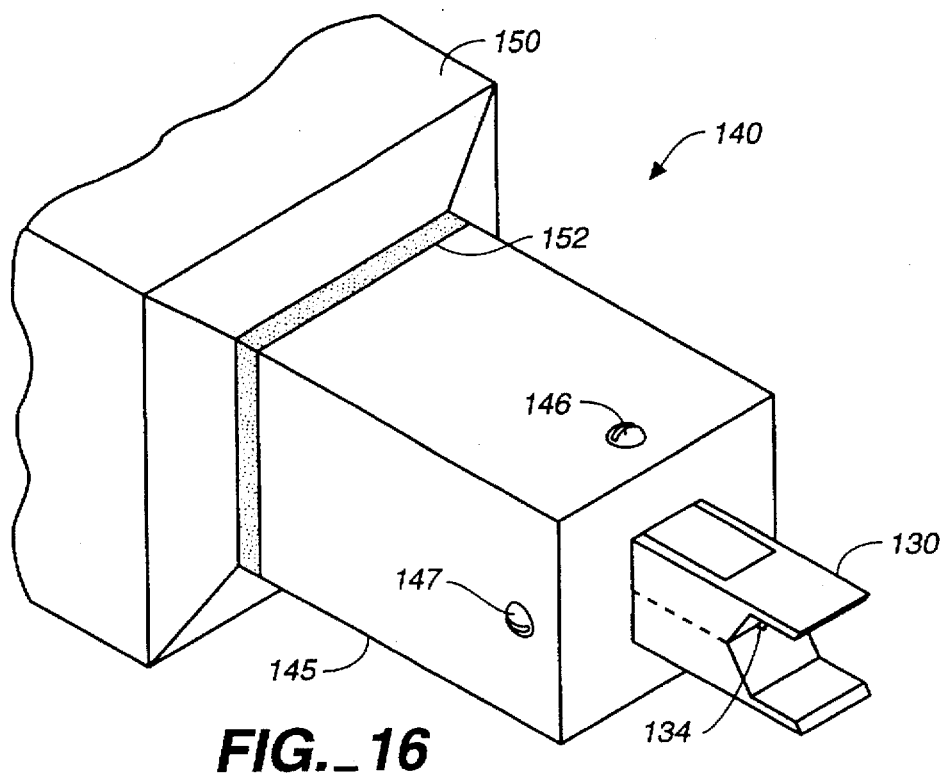
FIG._16
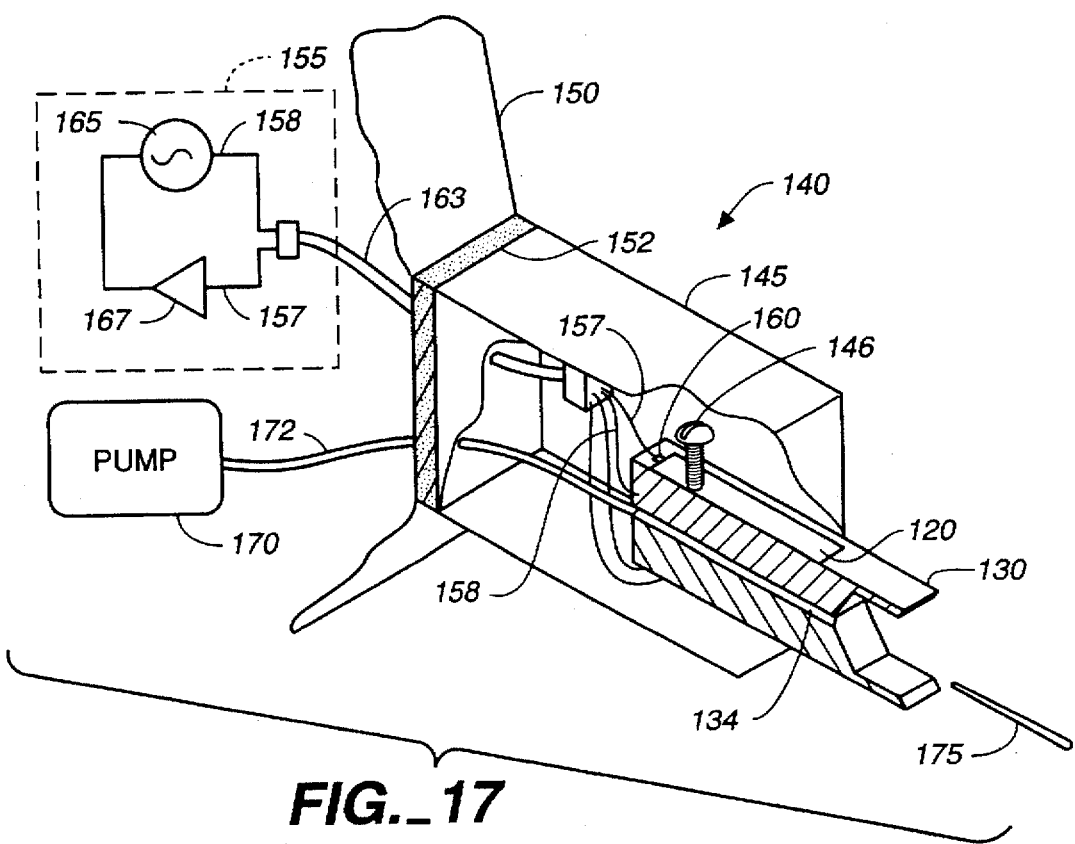
FIG._17

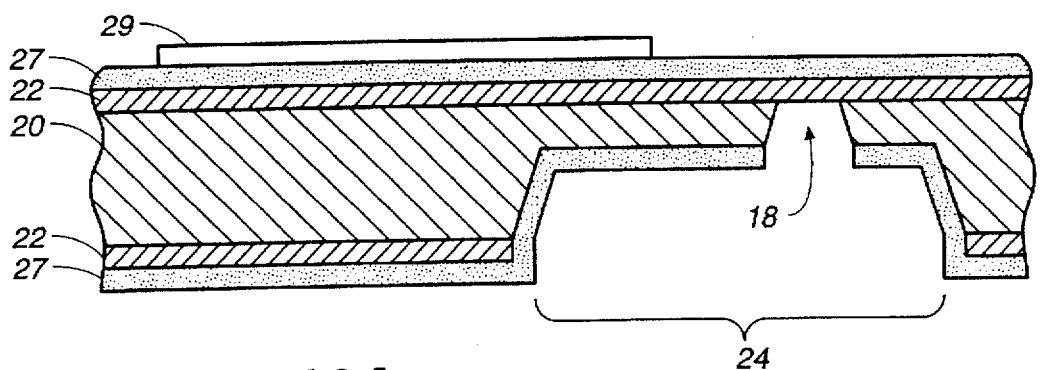
FIG._18A
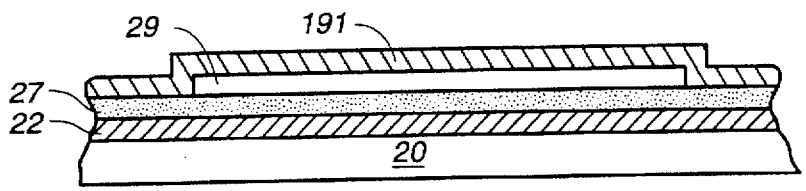
FIG._18B
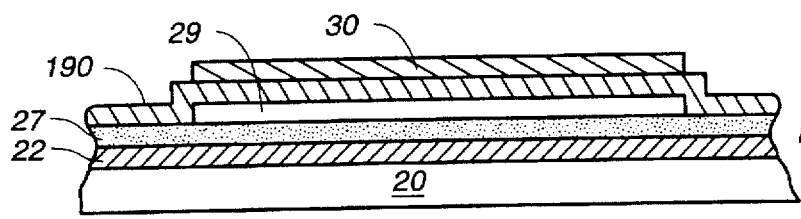
FIG._18C
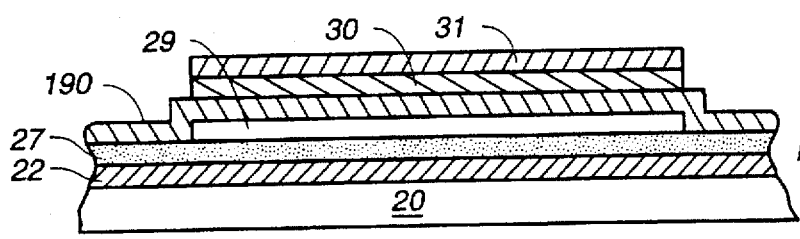
FIG._18D
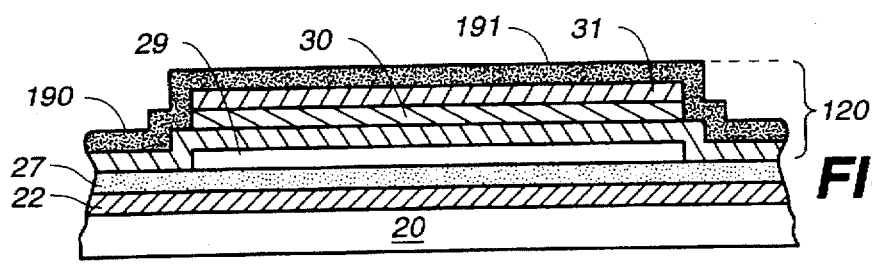
FIG._18E

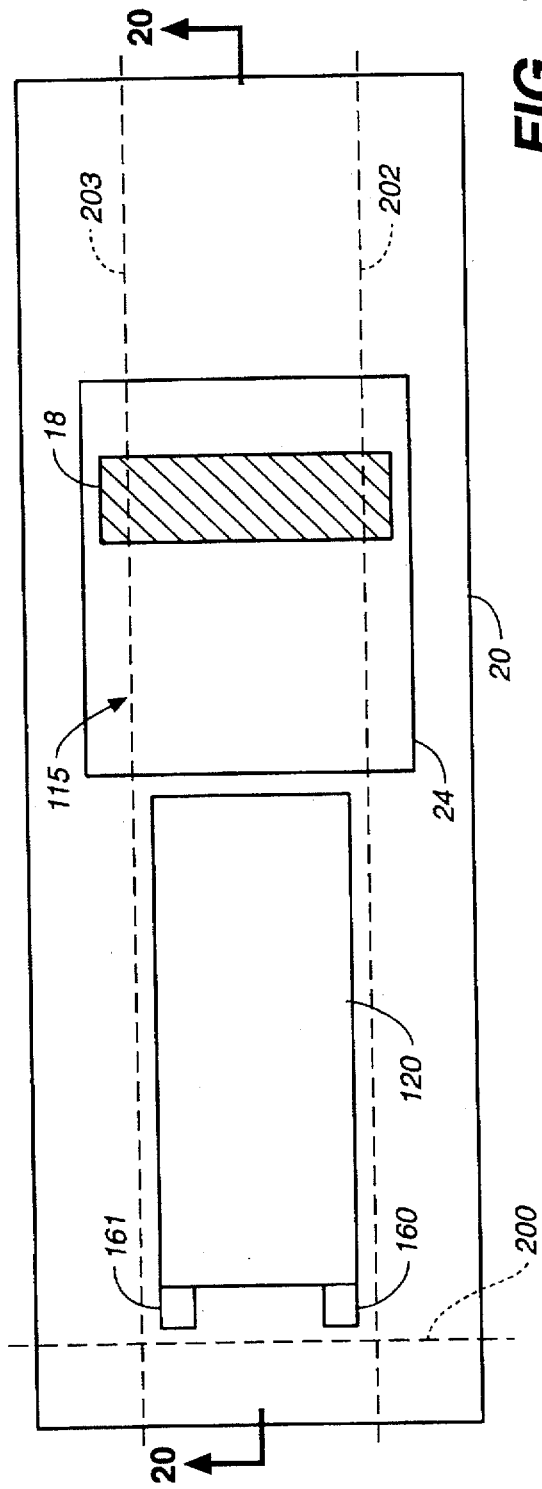
FIG._19
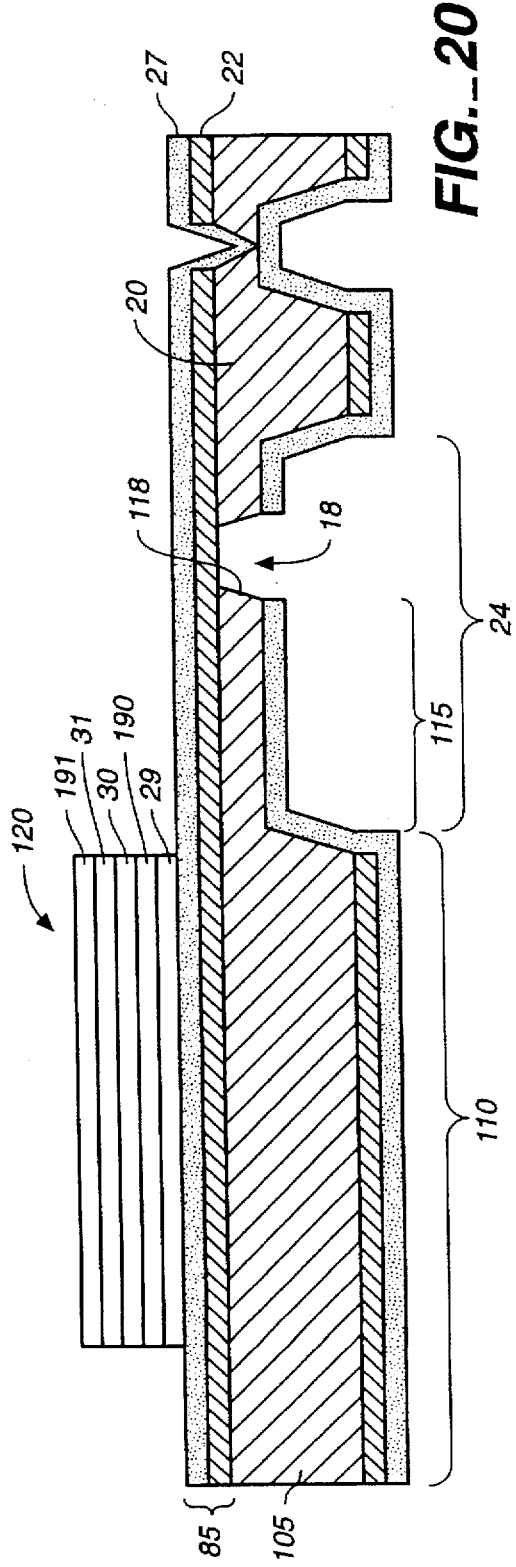
FIG._20

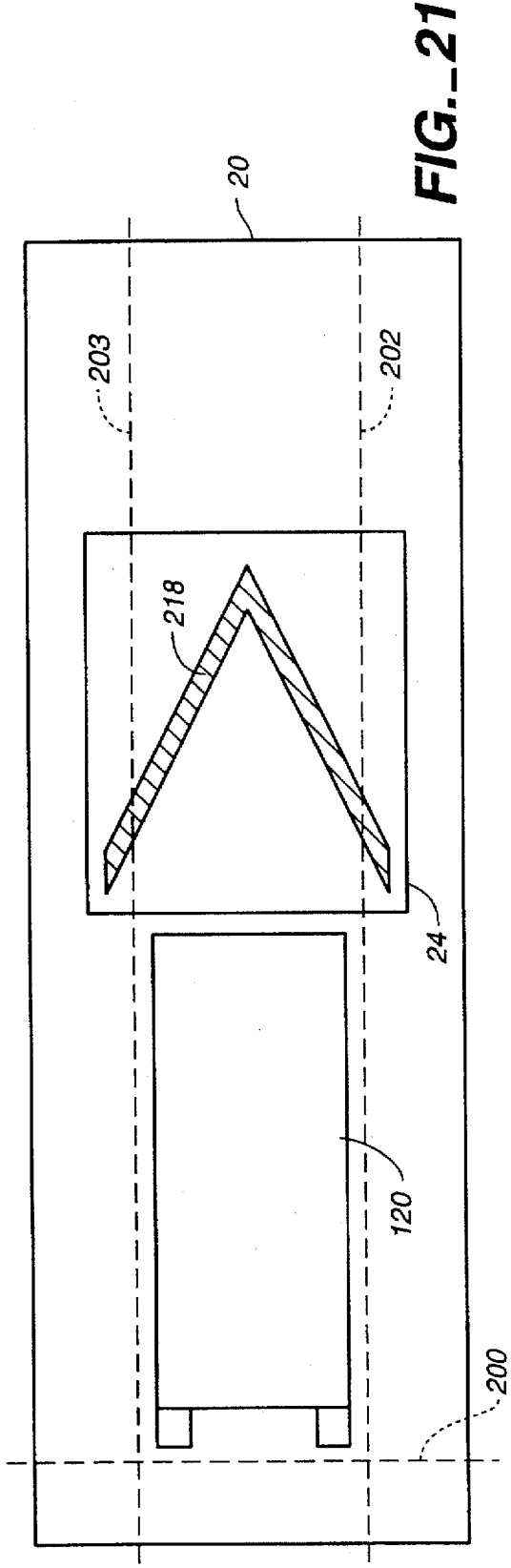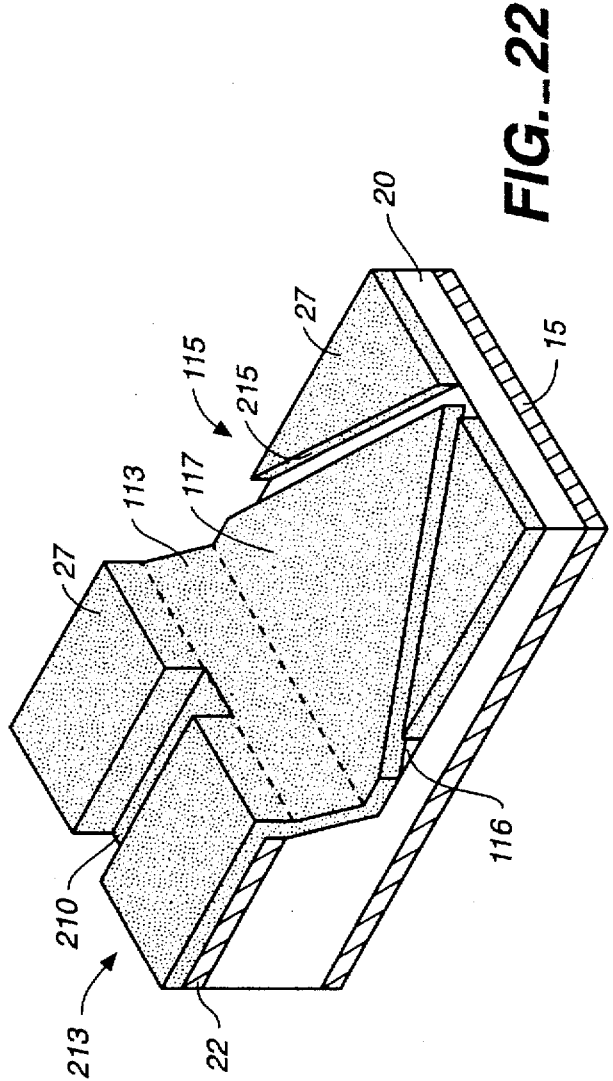

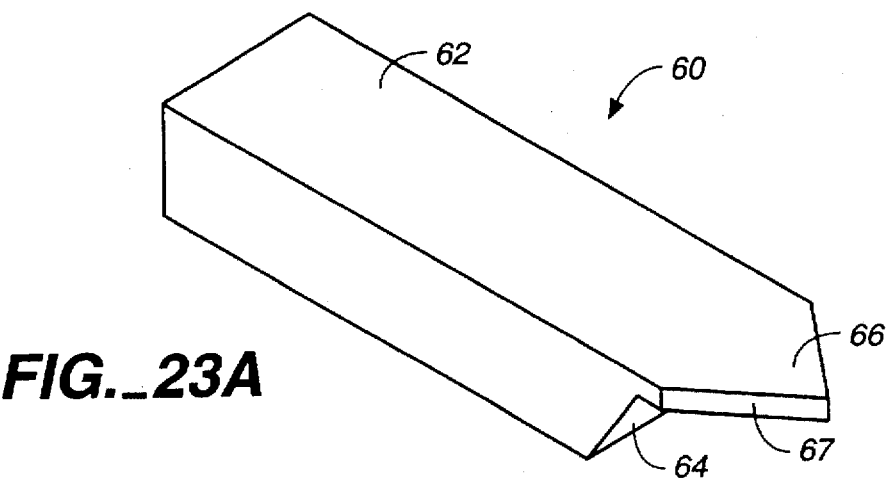
FIG._23A
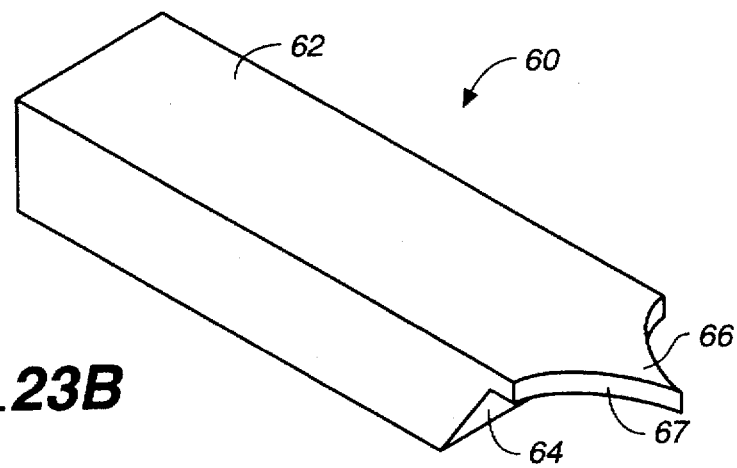
FIG._23B
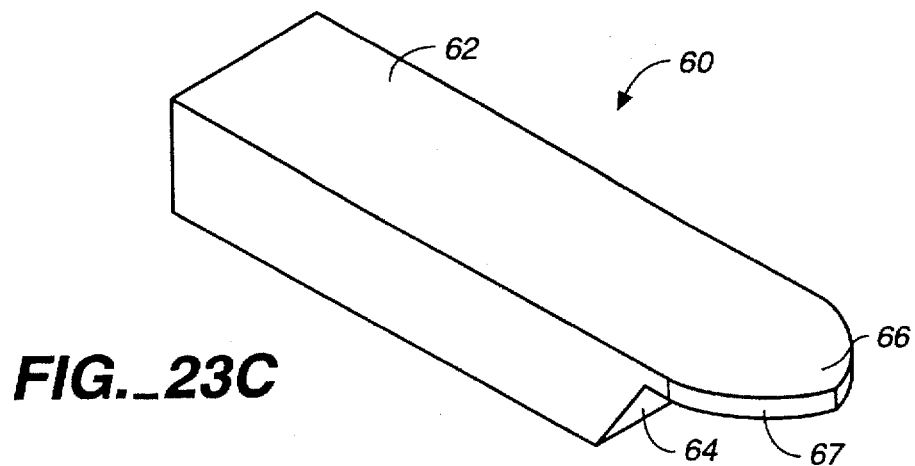
FIG._23C

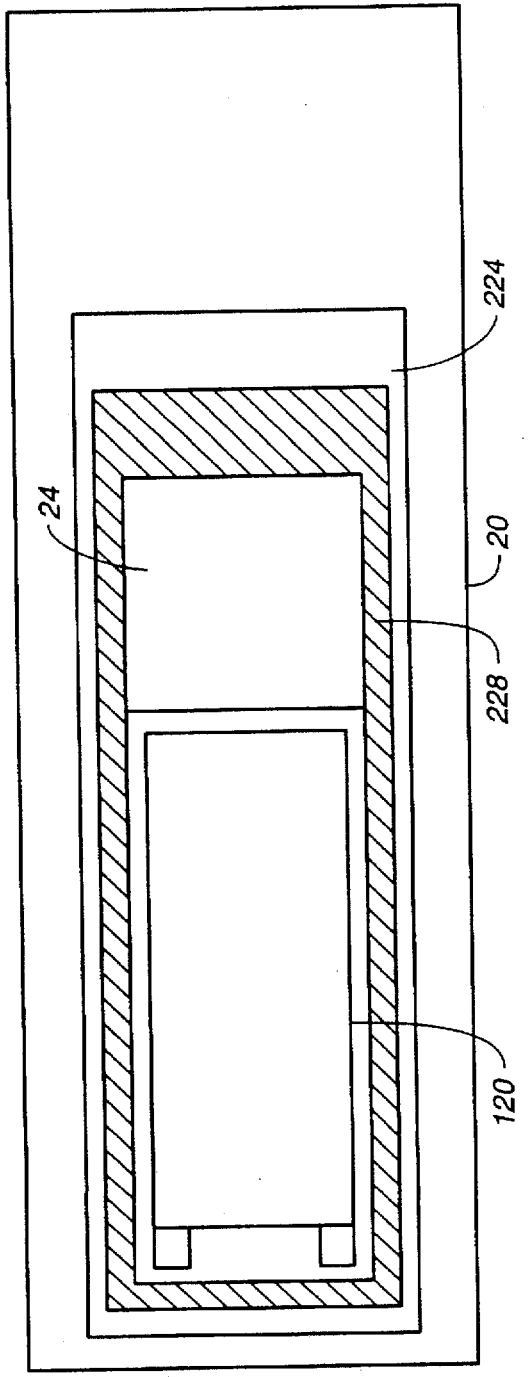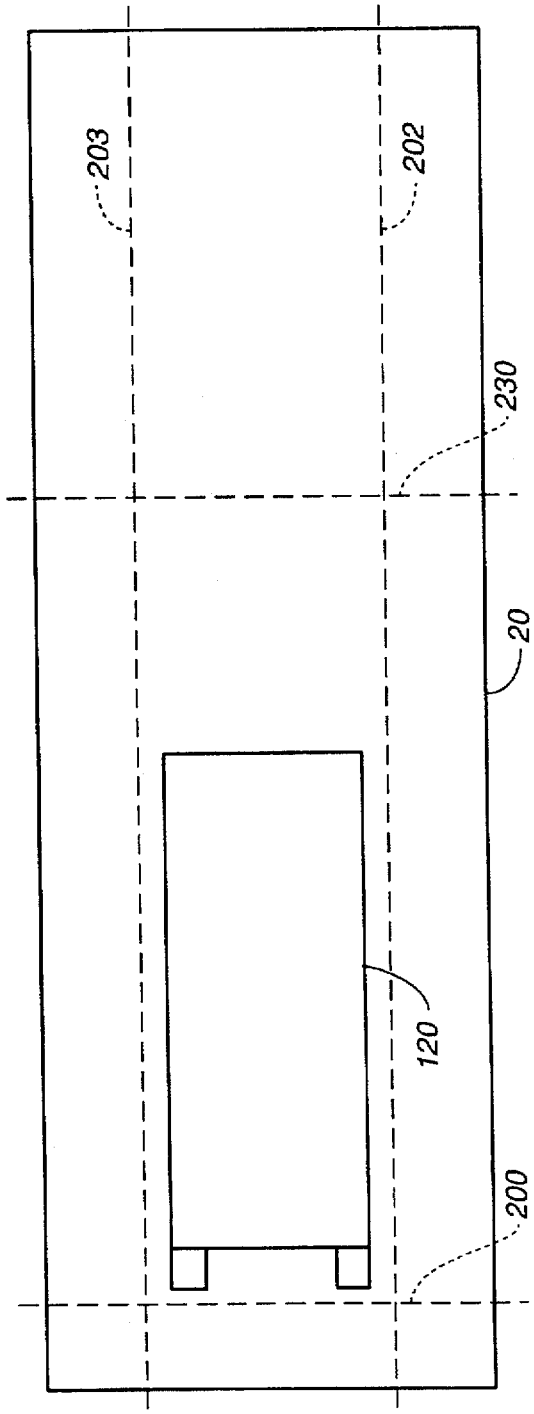

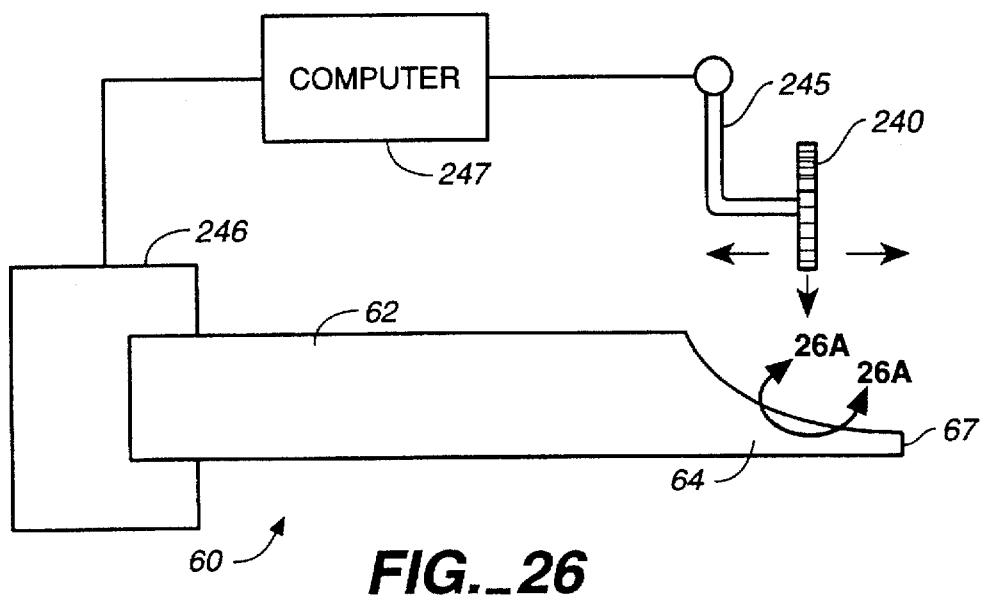
FIG._26
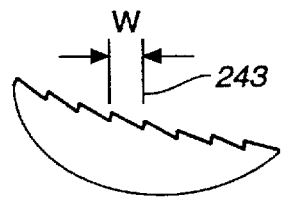
FIG._26A
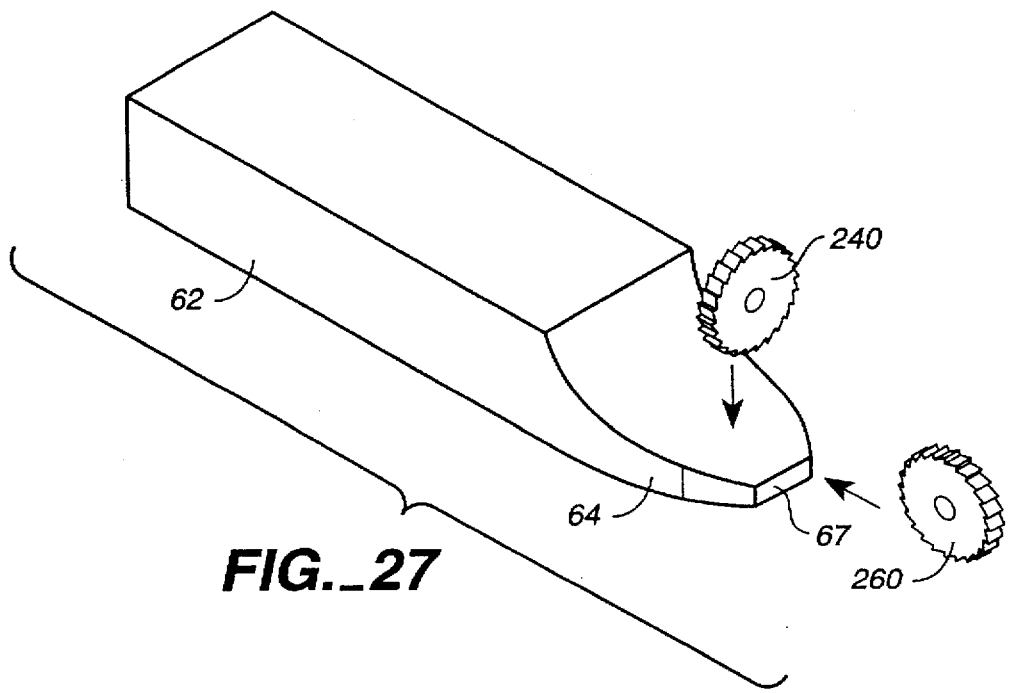
FIG._27

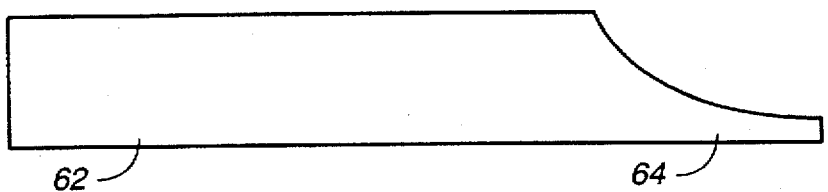
FIG._28A
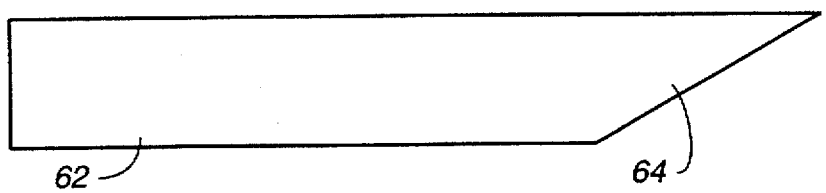
FIG._28B
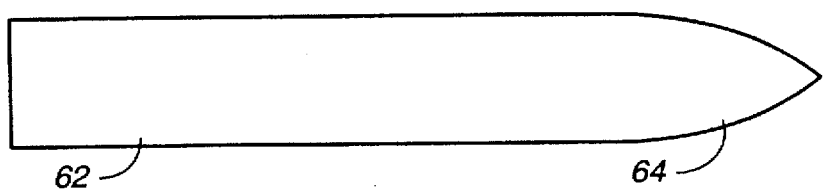
FIG._28C
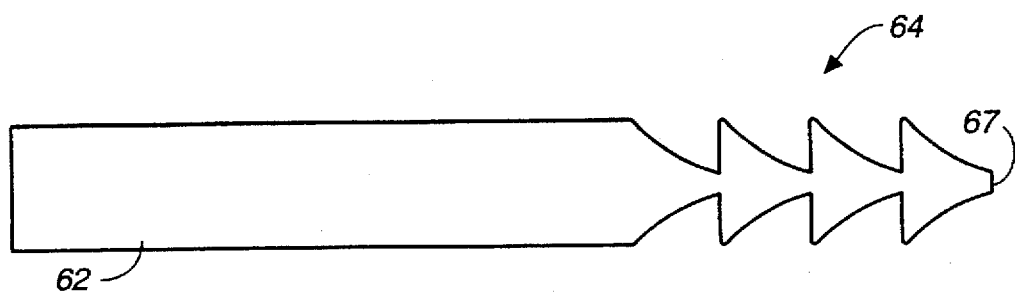
FIG._28D

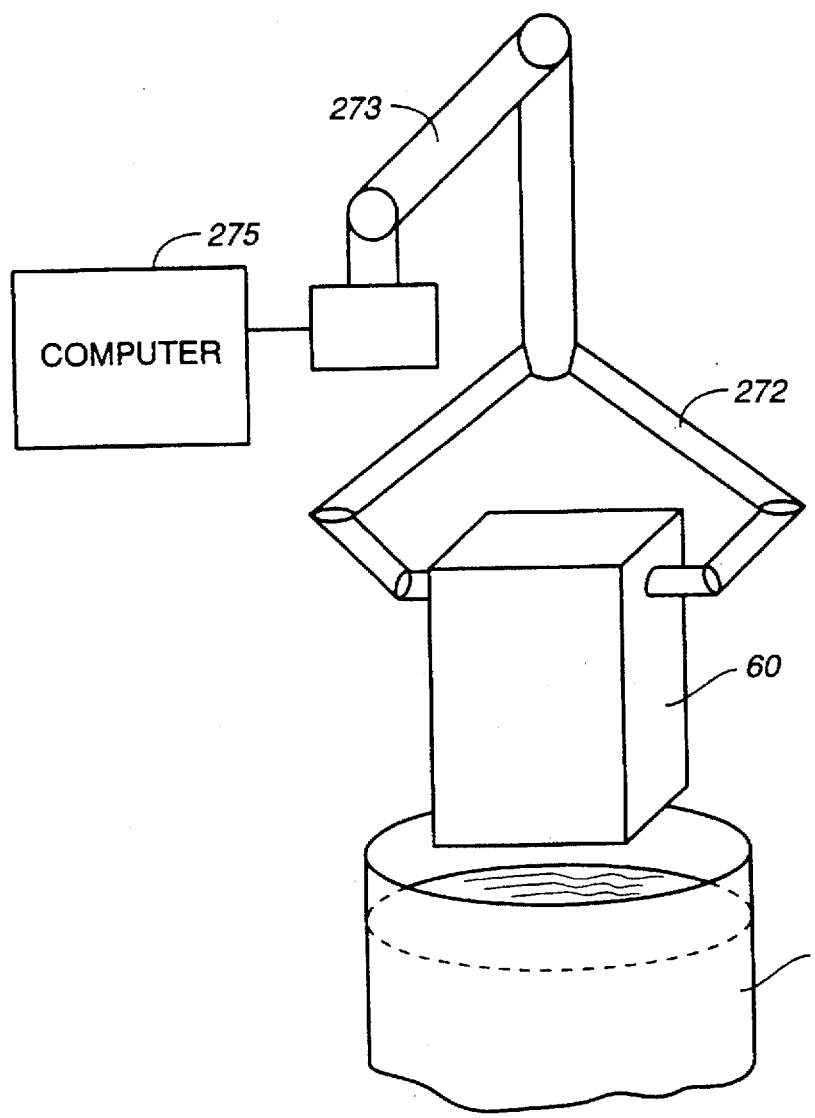
FIG._29
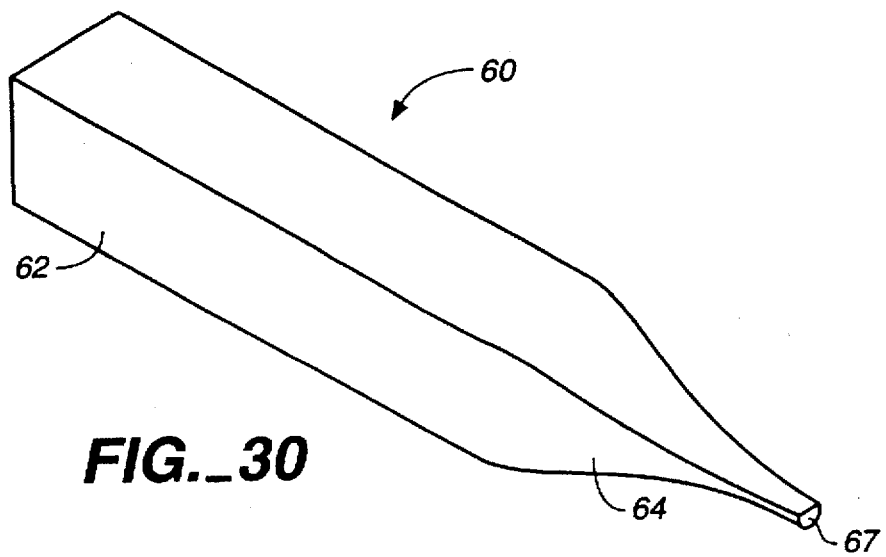
FIG._30

MICROFABRICATED STRUCTURE TO BE USED IN SURGERY

CROSS REFERENCES TO RELATED APPLICATIONS

This application is a continuation-in-part of application Ser. No. 08/306,843 filed Sep. 14, 1994, now U.S. Pat. No. 5,569,968; which is a continuation of abandoned application Ser. No. 08/072,294 filed on Jun. 4, 1993 (now abandoned).

STATEMENT OF RIGHTS

This invention was made with Government support under a National Science Foundation Grant awarded to the Berkeley Sensor and Actuator Center (BSAC). The Government has certain rights to this invention.

BACKGROUND OF THE INVENTION

In the field of surgical tools, there is a constant need for small high-strength devices for microsurgical applications. Miniaturized surgical tools are particularly useful in avoiding surgery where large incisions would otherwise be needed to remove tumors, e.g. in brain surgery. Yet another need is for high-precision microsurgical devices with high cutting power. Cutting power can be increased by making higher frequency excursions.

Current microsurgical tools are so expensive that they must be recycled. It would be desirable to have less expensive and disposable microsurgical tools. This would avoid the dangers of tool deterioration and failed sterilization that are inherent when using recycled surgical tools.

An additional problem with current microsurgical devices is cavitation. Cavitation is the formation of air bubbles when a solid object moves through a liquid. It is desirable to avoid the creation of air bubbles in the patient's body during an operation. Current microsurgical devices are likely to produce cavitation because they have a blade area which undergoes large motion at low velocity.

Another problem with microsurgical tools used previously is that they require a very high-voltage power supply. For example, previous microcutters may require about 1200 volts to operate. Such tools need cumbersome power cords and present the danger of high voltage discharge.

In the field of acoustic sources and receivers, current acoustic devices such as microphones are geometrically symmetric with little internal structure. They consist of rectangular or circular plates whose motions are detected capacitively, piezoelectrically, or piezoresistively. In its operating frequency range, mechanical response of such a device is a relatively smooth function of frequency. For more complex transfer functions, electronic filters must be used.

Micromachining, on the other hand, allows the fabrication of reproducible microstructures that have complex mechanical transfer functions. Complicating the mechanical designs simplifies the electronics which, in turn, can reduce required power and increase signal-to-noise ratio. Tools such as finite-element methods may be used to predict and tailor the response of a given device.

An object of the present invention is to provide a micromachined structure that may be used as a microcutter, microscraper or microhammer.

Another object of the present invention is to provide a microsurgical device suitable for surgical applications and having low power operation and which can be produced in batches at low cost.

Yet another object of the present invention is to provide a microcutter having a blade which makes small excursions at high frequency.

A further object of the present invention is to provide a microsurgical device which avoids cavitation.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to a structure suitable for use as a microsurgical implement and formed from a semiconductor substrate. The structure has a body and a horn projecting from the body. The horn has a blade portion which is free to vibrate and ends in a forward edge which is significantly thinner than the body.

The method of the present invention includes providing a semiconductor substrate and removing a significant thickness of material from the substrate to form a horn and a body in the substrate. The horn projects forward from the body and has a blade which is free to vibrate. The blade has a forward edge which is significantly thinner than the body. The blade may be covered with a hardened layer, for example, a diamond coating. The substrate may be silicon, and it may be covered with a silicon nitride membrane.

The structure may be attached as a needle at the tip of an oscillator. The structure of the present invention may include a piezoelectric actuator mechanically coupled to the body of the substrate. The piezoelectric actuator may be fabricated by thin film deposition onto the substrate, or it may be formed separately and bonded to the substrate.

Material may be removed from the substrate to form the horn by anisotropic backside etching, by liquid etching, or by making a series of cuts with a saw.

At high frequencies, the device can be used as a microcutter, microchisel or microhammer. The horn focuses mechanical energy from the body into the forward edge. This semiconductor structure can achieve higher velocities than prior metal structures. This may be important in the biological and medical industries for investigating and manipulating tissue, and holds the promise of better control and higher power in microcutting than other technologies such as laser cutting and ablation.

BRIEF DESCRIPTION OF THE DRAWINGS

The accompanying drawings, which are incorporated in and constitute a part of the specification, schematically illustrate preferred embodiments of the present invention, and together with the general description given above and the detailed description of these embodiments given below, serve to explain the principles of the invention.

FIG. 1A is a schematic representation of an acoustic source and receiver in accordance with the principles of the present invention.

FIG. 1B is a view along line 1B—1B in FIG. 1A.

FIGS. 2A–2I are process flow diagrams illustrating a process for fabricating an acoustic source and receiver of the present invention.

FIGS. 3A–3D schematically represent various microstructures that may be fabricated using the process illustrated by FIGS. 2A–2I.

FIG. 4 graphically represents the sound pressure level of a microstructure of the present invention.

FIGS. 5A and 5B are graphic representations of a microphone and speaker response, respectively, for the notch structure of FIG. 3A.

FIG. 6 is a graphical representation of displacement for the notch structure of FIG. 3A.

FIG. 7 is a graphical illustration of the speaker response of the cantilever microstructure of FIG. 3B.

FIGS. 8A–8L are graphical representations of the ABAQUS derived eigenmode shapes and eigen-frequencies.

FIG. 9 is a schematic representation of a circuit for an acoustic receiver functioning as a microphone.

FIG. 10 is a schematic representation of a circuit for an acoustic source functioning as a speaker.

FIG. 11A schematically illustrates a microstructure of the present invention used as a surgical cutter.

FIG. 11B illustrates the elliptical motion of the microstructure of FIG. 11A.

FIG. 11C is a schematic illustration of an alternative cutting edge of the cutter of FIG. 11A.

FIG. 12 is a schematic side view of a substrate constructed in accordance with the present invention.

FIG. 13 is a schematic view of an oscillator using the substrate of the present invention as a needle.

FIG. 14A is a schematic side view of a microstructure constructed in accordance with the present invention.

FIG. 14B is a schematic frontal view along line 14A–14B of FIG. 14A.

FIG. 14C is a schematic plan view along line 14C–14C of FIG. 14A.

FIG. 15A is a schematic perspective view of the an unassembled microcutter.

FIG. 15B is a schematic perspective view of two microstructures bonded together to form a microcutter in accordance with the present invention.

FIG. 16 is a schematic perspective view of a surgical tool of the present invention.

FIG. 17 is a schematic perspective and cut-away view of a surgical tool of the present invention.

FIGS. 18A–18E are process flow diagrams illustrating a process for fabricating a piezoelectric actuator according to the present invention.

FIG. 19 is a schematic plan diagram illustrating the step of cutting a silicon wafer to form a microstructure having a horn with a constant width.

FIG. 20 is a sectional view along line 20—20 of FIG. 19 after the silicon wafer has been cut.

FIG. 21 is a schematic plan diagram illustrating the shape of the window area at the step of cutting the silicon wafer in a microstructure having a horn with a tapered width.

FIG. 22 is a schematic perspective view of the backside of a silicon wafer at the step of removing the silicon nitride layer to form a substrate having a horn with a tapered width.

FIGS. 23A–23C illustrate various horn shapes that may be formed by back side etching.

FIG. 24 is a schematic plan view of the step of severing the microstructure from the wafer by using backside anisotropic etching.

FIG. 25 is a schematic plan view of the step of severing a microstructure from the silicon wafer by cutting with a saw.

FIG. 26 is a schematic side view illustrating the process of forming a horn of the present invention by cutting with a saw.

FIG. 27 is a schematic perspective view illustrating the process of forming a horn by cutting with a saw.

FIGS. 28A–28D are schematic diagrams showing the various horn shapes that may be formed by cutting with a saw.

FIG. 29 is a schematic diagram illustrating the process of fabricating a horn of the present invention by using a liquid etch.

FIG. 30 illustrates a horn that may be formed by liquid etching.

DESCRIPTION OF THE PREFERRED EMBODIMENTS

The present invention relates to a microfabricated acoustic source and receiver. This microstructure may function, for example, as a microphone or speaker at audible frequencies, and as a microcutter at ultrasonic frequencies.

The shape of the microstructure may be selected to produce a particular acoustic response. As shown in FIGS. 1A and 1B, an acoustic source and receiver 10 of the present invention may comprise interdigitated, transducer fingers 12 and 14. The fingers can be used to input mechanical energy into the microstructure. A piezoelectric ZnO layer sandwiched between aluminum planes, one of which serves as an electrical ground plane, may form the transducer fingers. By way of example, the aluminum planes may each be about 0.3 microns(μm) thick, and the ZnO film 2 microns thick.

Other transducer patterns and transduction mechanisms, other than piezoelectric, may be used. For example, the transduction mechanism may comprise a thermal stress, electrostriction, magnetostriction, or optical drive system.

Fingers 12 and 14 may function as sense or generating transducers. As will be described below in reference to FIGS. 10 and 11, if microstructure 10 functions as an acoustic receiver, for example a microphone, fingers 12 and 14 may both act as sense transducers. That is, no drive voltage (Vpp) is applied to the fingers, and stresses imparted to the microstructure will cause the transducers to generate an electrical signal. If, on the other hand, microstructure 10 functions as an output device or acoustic source, for example a speaker, a drive voltage Vpp may be applied to transducers 12 and 14. Alternatively, one transducer, for example transducer 12, may function as a sense electrode to provide feedback control, while the other transducer acts as a generating transducer to which the drive voltage is applied.

The transducer fingers may be formed on a thin silicon plate section 16 of a substrate 13 that also includes a frame or baffle section 17. The plate 16 may be between about 40 and 100 microns thick, and more preferably between about 50 and 70 microns thick.

A silicon nitride membrane or layer 15 may be formed between the fingers and plate 16. Layer 15 may be between about one and four microns thick, and more preferably about 2 microns thick. Membrane 15 may also be formed of other materials such as polysilicon, silicon dioxide or various polymers, and may comprise of sandwich materials of thin layers of many such materials.

The thickness of baffle section 17 may be between about 500 and 550 microns. The frame 17, like plate 16, may be formed of silicon. As mentioned, the frame and plate sections are part of a substrate that supports membrane 15, and transducers 12 and 14. Other materials may be used for plate 16 and frame 17. For example, quartz may be used to give the microstructure different elastic properties.

The microstructure 10 also includes a window section 18. Section 18 may be a silicon nitride film that is about 2 microns thick. The window section may be formed, as will be discussed, by removing material from preselected regions of plate section 16. As will be described, the location and pattern of the window section or sections can be selected to tailor the frequency response of the microstructure. As such, a desired frequency response may be designed for without the use of complex electronics.

The thin silicon plate configuration of microstructure 10, with very small area connecting silicon nitride, is much stronger than large-area thin membranes. Therefore, microstructure 10 can operate under very rugged conditions.

The fabrication of structure 10 may start with a four-inch silicon wafer 20. As shown in FIG. 2A, a 4000 angstrom(A) layer of low-stress silicon nitride 22 may be first deposited on the wafer in an LPCVD furnace. The nitride is patterned using lithography and plasma etching exposing the silicon areas 21 to be removed. As seen in FIG. 2B, a small square (or squares) 23 is opened on the top side for silicon membrane thickness control. The wafers are then etched in a KOH bath (FIG. 2C). The square is sized so that KOH etching ceases on the top when a certain height pyramid 26 is etched; much larger squares 24 etch on the backside concurrently. When the backside incomplete pyramid 25 encounters top pyramid 26, the transmission of light is observed and the wafer is removed from the etch bath. This method permits control of the silicon membrane thickness to within +/−5 microns.

Next, as shown by FIG. 2D, a second layer of ~1.5 μm thick silicon nitride 27 is deposited over the entire wafer. Backside lithography is used to remove this silicon nitride where additional silicon 28 is to be etched (FIG. 2E). The plate structure and window section 18 (see FIGS. 1A and 1B) is then defined by removing the silicon using KOH etching (FIG. 2F). The silicon nitride (layer 15), which, as noted, may be about 2 μm, is strong enough to support the silicon substrate members (plate 16 and baffle 17) and survive further processing steps.

The next steps (FIGS. 2G–I) involve making the piezoelectric transducer fingers 12 and 14. A 3000 A thick, aluminum layer with two percent silicon is sputtered on the front of the device. The sputtered aluminum is then patterned using PR lithography to form regions 29. A 2 μm thick film 30 of ZnO is then RF magnetron sputtered on the wafer. A second film 31 of aluminum is sputtered over the ZnO and is patterned by PR lithography to form the electrical ground plane. This aluminum pattern is then used as a mask to remove the exposed ZnO by etching, allowing electrical contact to the transducers to be made via aluminum regions 29.

FIGS. 3A–3D show various structures that may be fabricated using the process of FIGS. 2A–2I. These structures produce different frequency responses. The microstructures illustrated are a notch structure 32, a cantilever structure 34, and structures 36 and 38 with beams of different lengths and widths. The overall transverse dimensions "y" and "x" of the thin silicon plate 16 of these structures may be about 9 millimeter (mm) and 10 mm, respectively. The thickness of plate 16 is about 60 microns. These various designs were made to study the effect of beams and cantilevers of different lengths and widths. Transducers 12 and 14 in the shape of interdigitated fingers were used to excite very high-frequency (100 kHz and above) modes.

The window section 18 of notch structure 32, as shown in FIG. 3A, forms a simple notch in silicon plate 16 spanning two sections of the plate. The window section 18 of microstructure 34 (FIG. 3B) forms a cantilevered arrangement wherein transducers 12 and 14 are supported at one end 19 relative to plate 16. Microstructures 36 and 38 (FIGS. 3C and 3D) show beams of different lengths "l" and widths "w". For example, the lengths "l" of the beams may range from about 1 to 4 mm and the widths "w" from about 1 to 2 mm.

The following characteristics of the microstructures may be measured: sound pressure level, acoustic input/output response spectrum, and membrane deflection. Using a sound pressure level meter, the sound intensity of notch device 32 (FIG. 3A) was measured as a function of input voltage versus distance from the device. A pressure level of 85 dB was measured about 1 centimeter(cm) away from the device at its 9.7 kHz resonance. The device radiated sound isotopically because the wavelength of the flexural wave is much smaller than the acoustic wavelength in air at this frequency. FIG. 4 shows the output power level in dBs. As can be seen, the pressure produces a log-like curve which, when plotted in linear pressure units, indicates a linear function of the input drive voltage Vpp.

The acoustic output as a function of frequency was also measured for notch structure 32. A microphone was placed 0.5 cm above the center of the device to measure its output when a sinusoidal signal from 4 to 50 kHz at 1 Vpp was applied to the acoustic source. Similarly, the microphone response was tested by applying a calibrated acoustic signal from an external speaker (producing signals from 4 to 20 kHz) near the acoustic receiver and measuring the signal generated. The microphone response was 900 μV/μbar at 9.4 Khz and 160 μV/μbar at 5.7 kHz. The sensitivity was higher than 40 μV/μbar in the range of 6 to 11 kHz.

The displacement of notch device 32 was also measured using a laser-amplified feedback interferometer (see FIG. 6). The resolution of the interferometer system is −1 nanometer, well below the displacements measured. The quality factors of the resonances were found to range from 20 to 30. Since the thin silicon nitride moves as much as, if not more than, the silicon, the silicon nitride film can be used as a coupling agent between different silicon sections. The displacement at resonance reaches 100 nm (at 3 Vpp). The displacement was measured at various locations on the device in the frequency range of 10 Hz to 52 kHz to obtain an estimate of the mode shapes. The final goal, however, is to predict a response once a particular structure is given.

The notch structure 32 is complicated due to the asymmetry of the nitride window. The speaker response for the much simpler cantilever-microstructure 34 (FIG. 3B) is shown in FIG. 7. A B&K microphone was placed 1 mm away from the center of the cantilever to measure the radiated field. The dashed line represents the response in the presence of the silicon nitride window 18 connecting the silicon membrane to the frame. The heavy line shows the response with the nitride window removed. The two curves show that removing the nitride window shifted the response down by 2 to 4 kHz. Furthermore, the resonances with the nitride window are broader than those without it. This indicates that the nitride window can play a major role in determining the response of these devices: both as a coupling agent between silicon members and as a damping section, which dampens the resonance of the structure to provide a broader resonance.

To predict the response of a given microstructure, the elasticity theory specialized to layered plates coupled to a fluid such as air can be used. The cantilever structure 34 was modeled in ABAQUS, a finite-element mechanical analysis program. A 20×20 array of nodes was used with 10×10 shell elements. These shell elements consist of 9 nodes. Each shell element was modeled as a 65 μm thick silicon plate sandwiched between two 1 μm nitride membranes. The results of an eigenmode analysis appear in FIGS. 8A–8L, where the first twelve mode shapes and their respective frequencies are shown. Since the B&K microphone was located 1 mm above and near the center of device 34, with its sensitive area (~2 mm in diameter) much less than the device area, it is expected that modes that have substantial deflection at the center will contribute more to the measured response. Modes 4, 5, 8, and 12 (highlighted in FIGS. 7, 8D, BE, 8H, and 8L) have displacements that are effectively symmetric with respect to the center of the cantilever and produce large motion there in at least one of the directions. As expected, these are the same modes that match with the measured response.

The predicted frequencies are in agreement with the measured response given the resolution bandwidth of the measurement was 1 kHz. An error of about +/−500 Hz exists in modes 4, 5, 8, and 12. Mode 5 has an error of about 1.1 kHz. Wrong values for material properties (such as the Poisson's ratio for silicon) being entered for the model might be responsible.

In addition to predicting the frequency, a feeling for the relative amplitude at each frequency should be obtained. At large plate wavelengths, the plate looks like a piston which pushes against a large area of air and feels the maximum resistance. This also causes the output to be isotropic as there is no preferred direction. When many wavelengths fit in the plate, the air resistance is lowered as air displaced at one point easily pushes the plate on points half wavelength away as those points displaced in the opposite direction. This lowers the effective pressure. Radiation becomes anisotropic as the wave has a preferred angle of propagation. FIGS. 8A–8L show the mode shapes for each mode. The acoustic wavelengths in each direction of the plate can be estimated. As can be seen, modes 4 (FIG. 8D) and 5 (FIG. 8F) radiate well because they are essentially piston-like, while modes 8 (FIG. 8H) and 12 (FIG. 8L) do not radiate well because they have many maximums and minimums and are not piston-like.

A micromachined acoustic source and receiver has been described that can produce 85 dB sound pressure level (at 7 kHz and 3 Vpp drive) and 900 μV/μbar sensitivity at its resonant frequency. These frequencies lie in the acoustic and low ultrasonic ranges. A cantilever microstructure in a finite-element analysis using shell elements was modeled, which confirms that the elastic shell theory can be used to design a response.

The acoustic source and receiver shows promise in hearing aids and other applications where a compact acoustic source is required. A combination of speaker and microphone on one chip, integrated with other electronics, can be used to measure speed using the doppler effect, or can be used to measure distance. For hearing aid applications, the frequency response can be designed into the mechanical microstructure. Thus, a hearing aid custom-tailored for an individual may be fabricated. Furthermore, the transduction system described herein is mainly capacitive and therefore consumes very little power. This gives the opportunity to make the electronics simpler to reduce the power budget. In addition, unlike other micromachined microphone structures made of thin diaphragms and membranes, this device is made of a relatively thick silicon plate 16 supported by very thin silicon nitride membranes (windows) that can withstand harsh environments.

The use of a microstructure, in this example cantilever structure 34, as an acoustic receiver, for instance a microphone, is shown in FIG. 9. The transducers 12 and 14 both act as sense electrodes whose output is applied to amplifiers 40 and 41, respectively.

A circuit for an acoustic source is shown in FIG. 10. The source, for example, may function as a speaker or cutter. A voltage source 42 is connected to an impedance matcher 44 through an amplifier 43. The output of the impedance matcher, drive voltage Vpp, is applied to generating transducer 14. Transducer 12 acts as a sense transducer for a feedback loop including amplifier 45 and feedback circuitry 46. The feedback loop can control the frequency response and the amplitude of motion of the microstructure.

Alternatively, as shown by dashed line 48 in FIG. 10, both transducers 12 and 14 may act as generating transducers when the microstructure functions as a source. In this embodiment, the feedback loop would be eliminated.

It is also possible to connect the microstructure of the present invention in a circuit so it functions both as a source and a receiver. That is, for example, it may act as both a microphone and speaker at audible frequencies.

As discussed, the fabrication process allows for the fabrication of thin transparent film sandwiches that can act as windows 18 (see FIGS. 1A–1B). When a mechanical vibration (bending) is applied to the microstructure, stresses may cause a change in transmittance and index of refraction of the thin film. A change in index of refraction and absorption properties (elasto-optic properties) of the window section can be used to modulate and/or deflect light.

As an optical device, the microstructure of the present invention can provide inexpensive phase plates in optical systems which are shrinking in size due to requirements of larger number of optical components in a small package and portability of such systems.

At ultrasonic frequencies, plate modes in the structure can be excited. Thus, an open-ended plate 50 can be used as a cutter (see FIG. 11A). The cutter may be fabricated as described above and include interdigitated transducers 52 and 54. The cutter may include an angled cutting edge 55. The angle θ of the cutting edge can be about 57.3°. An ultrasonic, flexure wave generated at one end of the cutter will travel to cutting end 55, producing an elliptical motion 58 as shown in FIG. 11B. This motion can be used to cut soft materials such as tissue. Since the zeroth order antisymmetric Lamb mode has a phase velocity less than that of sound in water, acoustic energy will be trapped in the plate while that motion cuts at the cutting end. An alternate cutting edge 56 for the microcutter is shown in FIG. 11C. This edge incorporates a beak-like configuration.

As a cutter, the present invention holds the promise of cutting biological tissue when treating diseases like cataracts (the most-performed operation in the United States), clogged arteries and neural tumors. Splicing cells and cutting tissue precisely can be very useful technologies for the medical and biological industries.

The present invention is directed to the use of a silicon substrate as a vibrating surface. An advantage of the present invention is that a silicon device can achieve greater velocities than prior metallic alloys in surgical instruments. Most prior art vibration devices use a titanium alloy. In general, the maximum velocity of a material is approximately equal to the strain on that material times the speed of sound in that material. The speed of sound in titanium alloy is approximately 42 meters per second, whereas the speed of sound in silicon is approximately 335 meters per second. Therefore, a device constructed of silicon should be able to achieve velocities approximately eight times greater than those of titanium or other metallic alloys. An additional benefit of silicon devices is that they may be fabricated by thin film techniques and machine worked, whereas metallic devices can only be machine worked. The present invention involves the use of a silicon substrate to take advantage of these physical characteristics.

A mirco-surgical device in accordance with the present invention may include a silicon substrate used as a needle attached to an oscillator. Alternately, a piezoelectric actuator may be attached to a silicon substrate to provide mechanical energy for microsurgery.

FIG. 12 shows a substrate 60 having a body portion 62 and a horn portion 64. It is preferred that substrate 60 be silicon, although substrate 60 may be another non-metalic material with equivalent properties. Other crystalline semiconductors may be suitable. Body portion 62 and horn portion 64 are preferrably the same material.

Extending from horn portion 64 is a blade portion 66 having a forward edge 67. Blade portion 66 is free to vibrate, and will be the primary surface used in cutting, scraping, or other microsurgical applications. Body portion 62 may serve either as a means for storing mechanical energy or as an attachment spot where mechanical energy may be input from an external device. In either case, mechanical energy will be focused through horn 64 to blade portion 66 and forward edge 67. The shape of horn portion 64 determines the mechanical-acoustic properties, such as the maximum velocity and vibrational mode, of blade portion 66 and forward edge 67. In the present invention, horn portion 64 maximizes the velocity of blade portion 66. Possible shapes for horn portion 64 will be discussed in greater detail below. However, horn portion 64 should generally be tapered in shape, narrowing from the thicker body portion to the thin forward edge. Blade portion 66 should be sufficiently thinner than body portion 62 so forward edge 67 takes advantage of the increased velocity available in silicon.

As noted and shown in FIG. 13, silicon substrate 60 may be used as a needle attached to an oscillator 70. In this context, a needle is a general instrument attached at the end of an oscillator (not part of a syringe). A needle may serve as a cutter, hamer, or scraper. Oscillator 70, as well known in the art, may be composed primarily of a titanium alloy and include a piezoelectric donut 71. An extremely high voltage, for example 1200 volts, is applied across piezoelectric donut 71 to cause it to oscillate. The mechanical energy is transmitted through metallic horn 72 to substrate 60 which forms the needle. Body portion 62 of substrate 60 is secured to oscillator 70 with a bond 73. Bond 73 may be a glue or it may be a nut and bolt arrangement. In operation, mechanical energy is transmitted through bond 73 and body portion 62, and is focused by horn portion 64 in forward edge 67. Because substrate 60 is composed primarily of silicon, forward edge 67 may reach a higher maximum velocity than a metallic needle.

Referring back to FIG. 12, depending on the shape and the vibrational mode of forward edge 67, substrate 60 could be used for a variety of different purposes. If forward edge 67 has a sharp edge and moves up and down with reference to surface 76, then the silicon substrate 60 may act as a microscraper to scrape material off of surface 76. If forward edge 67 has a sharp edge and moves forward and back with reference to surface 76, then silicon substrate 60 may act as a cutter to cut into surface 76. For example, surface 76 could be brain tissue which a surgeon must cut to remove a neural tumor. If forward edge 67 is blunt and moves forward and back with reference to surface 76, then silicon substrate 60 may act as a microhammer to emulsify surface 76. For example, surface 76 could be a cataract which a surgeon will emulsify.

As a microscraper, microhammer, or microcutter, blade portion 66 should have a hardened edge. A hardened layer 80 may cover the entire substrate 60, but it is only necessary for the active portion which contacts surface 76, i.e., the blade portion 66. Blade portion 66 may be coated diamone or silicon carbide using conformal vapor deposition to form hardened layer 80. Alternately, blade portion 66 may be implanted or doped with carbon, boron or phosphorous to form hardened layer 80.

A membrane 85 may be disposed on an outer surface of substrate 60. The presence or absence of membrane 85 depends on the processing steps utilized in the formation of the substrate 60. The membrane 85 will usually be a silicon nitride layer approximately 1–4 microns (µm) thick. If membrane 85 is present, then it will be on the top surface of body portion 62 and horn portion 64.

As noted and as shown in FIGS. 14A, 14B and 14C, a microstructure 100 of the present invention may comprise a semiconductor substrate 105 and a mechanically coupled piezoelectric actuator 120. Substrate 105 is similar to substrate 60, but references to substrate 105 indicate that it is preferred a piezoelectric actuator to be attached. The substrate 105 may have a thick body portion 110 and a thinner horn portion 115. Substrate 105 may include a hardened layer 80 and a membrane 85, but these items are not shown in FIGS. 14A–C for ease of illustration. Horn portion 115 may be tapered in a narrowing portion 119 to a blade portion 117, which ends in a forward edge 118. Blade portion 117 should be the portion of substrate 105 which will make contact with the surface operated on in order to, for example, perform scraping, cutting, or emulsification. Forward edge 118 will be sharp if microstructure 100 is to be used for microcutting or microscraping applications, whereas forward edge 118 will be blunt if microstructure 100 is to be used for microhammering applications. Horn portion 115 focuses mechanical energy from body portion 105 into forward edge 118. Therefore, blade section 117 may act as an active surface while body portion 110 acts as an ultrasonic energy storage resonator.

Mechanically coupled to substrate 105 is a piezoelectric actuator 120. Piezoelectric actuator 120 resonates microstructure 100 to produce displacements in blade portion 117 for microsurgical applications. Piezoelectric actuator 120 may be formed by thin film deposition processes as part of the same process that creates substrate 105. Alternately, piezoelectric actuator 120 may be formed separately and attached to substrate 105 by a bonding agent.

As shown most clearly in FIG. 14B, substrate 105 may include a channel 125 cut into the bottom surface of body portion 110. The channel 125 runs from the front to the back of microstructure 100. Channel 125 may be about 50–100 µm deep and be formed by anisotropic etching as explained below.

As shown most clearly in FIG. 14A, microstructure 100 has two modes of vibration. Microstructure 100 has longitudinal resonant modes in which blade portion 117 vibrates forward and backward, and flexural resonant modes in which blade portion 117 vibrates up and down. The modes of vibration may be determined by the shape of horn 105 and the frequency of the applied voltage. Each mode of vibration has its own resonant frequency. In the preferred embodiment, the length and thickness of microstructure 100 are selected such that the fundamental longitudinal resonance and flexural resonance of microstructure 100 have the same resonant frequency. This increases the total energy stored in the resonator and maximizes the motion of forward edge 118. A typical resonant frequency is about 100 kilohertz (kHz). Making one resonant frequency an integer multiple of the other frequency will serve the same purpose, albeit less efficiently.

In one embodiment, body portion 110 is between about 20 and 40 millimeters (mm) long, more preferably 25 mm long. If substrate 105 is to be used as a needle attached to an oscillator, body portion 110 may be 50 mm long. Body portion 110 may be approximately 1 to 2 mm wide. Narrowing section 119 has a flat upper surface, a sloped bottom surface, and flat sides. Narrowing portion 119 may be approximately 200 to 300 µm long. Blade portion 117 is rectangular in shape, has the same width as body portion 110, and has a length of approximately 1 to 3 mm. However, as will be explained below, horn portion 115 and blade portion 117 may have other shapes.

Forward edge 118 and blade portion 117 should be significantly thinner than the body portion 110, so that body portion 110 acts as a resonator that stores energy while blade portion 117 vibrates to cut or emulsify the target. For example, the thickness of blade portion 117 should be 20% of the thickness of body portion 110, and more preferably only about 5%. On the other hand, blade portion 117 cannot be too thin; otherwise it, would lack the necessary structural strength to be a surgical tool. Body portion 110 may be 500 to 600 µm thick, while blade portion 110 is 50 to 100 µm thick.

As shown in FIG. 14A, blade portion 115 projects forward from the front end of body portion 110, and the top surfaces of body portion 110 and horn portion 115 form a single planar area. If substrate 105 includes a membrane 85, then membrane 85 may be disposed over the planar area. This configuration is simply one possible shape of horn 115 and is not necessarily preferred.

Piezoelectric actuator 120 may be disposed onto membrane 85 (as shown in FIG. 2I). If membrane 85 is absent, then the actuator may be disposed directly onto the substrate 105. It is preferred that piezoelectric actuator 120 overlay only body portion 110 so that horn portion 115 may be a variety of different shapes. Piezoelectric actuator 120 may include a first electrode layer, a layer of piezoelectric material, and a second electrode layer.

As shown in FIGS. 15A and 15B, a microcutter 130 for microsurgical applications may be assembled from two bonded microstructures 100a and 100b. Microstructures 100a and 100b may be identical to microstructure 100. After microstructures 110a and 110b are cleaned, microcstructures 100a and 100b are aligned, and the bottom surfaces of the body portions of the two substrates are fusion bonded by heating microstructures 100a and 100b to a high temperature at a high voltage. Alternatively, the microstructures may be bonded by melting a layer of aluminum between the substrates, or the microstructures could be bonded with a glue. Channels 125a and 125b are aligned so that when microstructures 100a and 100b are bonded, channels 125a and 125b form a single conduit 134. Conduit 134 runs from the front to the back of microcutter 130.

As shown in FIGS. 16 and 17, in a surgical tool 140 constructed according to the present invention, microcutter 130 is solidly mounted in a casing 145. Mounting screws 146 and 147, located at a vibrational velocity node of microcutter 130, hold microcutter 130 in casing 145. Other forms of mounting such as springs or glue might also be used. Casing 145 may be connected to a grip 150 with a locking connector 152.

In FIG. 17, the electrodes of the piezoelectric actuators of microstructures 100a and 100b are connected to a power supply 155. Electrical leads 157 and 158, are connected inside casing 145 to contact pads 160 and 161 (shown in FIG. 19) of actuator 120. Power supply 155 includes a voltage source 165 and an amplifier 167. Power supply 155 may be located inside grip 150 or it may be an external source. Power supply 155 may have a controllable frequency and voltage so that the frequency and amplitude of vibration of the forward edges of the microcutter 130 may be controlled.

Surgical tool 150 may include a pump 170. Pump 170 is connected to the back end of conduit 134 by tubing 172. Pump 170 may be located either inside grip 150 or externally. Pump 170 allows for the removal of debris generated during an operation by providing suction through tubing 172 so that debris is sucked in through conduit 134. Surgical tool 140 may also be provided with a needle 175. Needle 175 may be inserted into conduit 134 in order to dislodge stuck debris.

Microstructure 100 may be formed by the process previously described for constructing an acoustic source or receiver. In particular, horn portion 115 including blade portion 117 and narrowing portion 119 may be formed by utilizing the steps shown in FIGS. 2A through 2F. In particular, the step of etching wafer 20, shown in FIG. 2C, will create a thin preselected area 24 in the wafer. As shown in FIG. 18A, this thin area of wafer 20 will become blade portion 117, and the unetched part of wafer 20 will become body portion 110. By etching only the backside of wafer 20, the top surface of horn portion 115 and the top surface of body portion 110 form a single planar area. Other methods to form horn portion 115 will be described below. However, this process is particularly suited for construction of microstructure 100 by thin film deposition.

As shown in FIG. 18A, a first electrode layer 29 may be deposited onto silicon nitride layer 27. Although electrode layer 29 may consist of two interdigited electrodes, as shown in FIG. 9A, for use in a surgical tool it is preferred that electrode layer 29 be a single continuous layer. In addition, rather than being disposed entirely on blade portion 117, electrode layer 29 is disposed partially over body portion 110, and partly over blade portion 117 as shown in FIG. 18A, or, preferably, only over body portion 110, as shown in FIG. 14A.

Piezoelectric actuator 120 may be formed by thin film deposition as shown in FIGS. 18A–18E. Following the deposition of electrode layer 29, a passivation layer 190 is formed from a low temperature oxide (LTO) such as silicon oxide ($SiO_2$) approximately 0.2 µm thick (FIG. 19B). Then piezoelectric film 30 is deposited (FIG. 19C), followed by second electrode layer 31 (FIG. 19D). Finally, another passivation layer 191 is deposited (FIG. 19E). The patterning steps have been omitted from FIGS. 18A–18E, and may be performed in any manner known in the art. Passivation layers 190 and 191 may be required to provide insulation and prevent shorts between the electrodes 29 and 31, if electrodes 29 and 31 contain impurities. Passiviation layers 190 and 191 may conform to electrodes 29 and 31, or they may extend onto membrane 85.

There are three primary processes which may be used to shape horn 115 of substrate 105. These processes are: cutting with a saw, anisotropic backside etching, and liquid etching. These processes may be combined in order to form a horn of the desired shape.

Turning now to FIGS. 19 and 20, a process for forming the microstructure 100 with a horn 115 with constant width shown in FIGS. 14A–14C, will be described. Silicon wafer 20 is patterned and etched as previously described with reference to FIGS. 2A–2F by etching a region 24 and then etching a window 18 inside region 24. In the process illustrated in FIG. 19, piezoelectric actuator 120 is disposed by thin film deposition according to the steps taught with respect to FIGS. 18A–18E. Silicon wafer 20 may contain multiple areas, with each area containing an etched region 24, a window 18, and a piezoelectric actuator 120.

As shown in FIG. 19 following the deposition of piezoelectric actuator 120, the piezoelectric actuator 120 is patterned to open up contacts 160 and 161.

Then silicon substrate 105 is separated from silicon wafer 20. Specifically, wafer 20 is cut with a saw along cut lines 200, 202, and 203. The saw may be a high speed saw with a diamond coated edge and a blade thickness of about 50 to 100 µm, such as a Disco™ saw. The cut lines may be selected so that the flexural and longitudinal resonances of the substrate 105 are equal. Cut lines 202 and 203 may be very close to piezoelectric actuator 120 so that the substrate 105 is not significantly wider than the piezoelectric actuator and the entire width of substrate 105 acts to store mechanical energy. For example, substrate 105 may be up to 10 percent wider than piezoelectric actuator 120. Cut lines 202 and 203 should pass through window area 18. The location of cut line 200 should be selected so that the piezoelectric actuator 120 lies in the middle of the body portion 110.

As shown in FIG. 20, once wafer 20 is cut using the silicon saw, substrate 105 remains attached to wafer 20 by the small portion of membrane 85 overlying window area 18. Microstructure 100 may then be entirely detached from substrate 20 by severing the portion of membrane 85 which lies above window area 18. Preferably, membrane 85 may be snapped simply by applying physical pressure to substrate 105. Alternately, membrane 85 may be cut with a silicon saw or membrane 85 may be removed by a plasma etch. The anisotropic etch of window 18 provides a sharp forward edge 118 when membrane 85 is severed.

Piezoelectric actuator 120 may be formed separately and then bonded to substrate 105. In this case, wafer 20 would still be patterned by etching a region 24 and then etching a rectangular window area 18 inside region 24. Rather than receiving thin film layers, wafer 20 would then be cut immediately with a silicon saw. The location of cut lines 200, 202, and 203 would be selected to accommodate the expected position where piezoelectric actuator 120 will be attached. Cut lines 200, 202 and 203 may also be selected to insure that the flexural and longitudinal resonances of substrate 105 are equal.

Anisotropic etching may be used to form horns of various shapes and, in particular, backside anisotropic etching may allow fine control of the width of the blade portion 117 of horn 115. In addition, backside anisotropic etching may be utilized to form channel 125. FIGS. 21 and 22 show the process steps in the creation of a microstructure 100 having a triangular front edge 118 and channel 125. In FIG. 22, after the second layer of silicon nitride 27 is deposited over the entire wafer 20, backside lithography removes the silicon nitride where silicon wafer 20 is to be etched. The silicon nitride is removed in a line 210 located on the bottom surface 213 of the thick portion of the wafer 20. When the silicon underneath area 210 is etched, channel 125 will be formed. Silicon nitride may also be removed along lines 215 and 216 located on the bottom surface of the thin portion of the wafer 20. When the silicon underneath areas 215 and 216 is etched, arrow-shaped window portion 218 in region 24, as shown in FIG. 21, will be formed. When microstructure 100 is detached from wafer 20, horn portion 115 will have a triangular front edge 118.

Blade portions 117 having a variety of different shapes, as shown in FIGS. 23A–23D, may be formed by using this process. The various shapes of blade portion 117 of horn 115 will influence the transfer of mechanical energy from body portion 110 to front edge 118. Although the mechanical-accoustic properties of a horn structure may be calculated by utilizing equations well known in the art, such calculations are mostly useful for horns with simple, idealized shapes. The present invention allows for easy construction of horns with complicated shapes which may have improved mechanical properties.

In the process for forming microstructure 100 as described with reference to FIGS. 19–22, both anisotrophic etching and cutting with a saw were used to define the shape of horn portion 115 and to sever substrate 105 from the wafer 20. However, either anisotrophic etching alone, or cutting with a saw alone, may shape horn portion 115 and sever substrate 105 from wafer 20. FIG. 24 shows the use of backside anisotropic etching to sever substrate 105 from wafer 20. During the first etch of wafer 20 (FIGS. 2A–2C), a region 224 which entirely surrounds what will become substrate 105 is etched. During the second etch (FIGS. 2D–2F), all of the silicon wafer may be removed in window 228 which entirely surrounds substrate 105. Substrate 105 remains attached to wafer 20 on all sides by membrane 85.

Instead of using anisotropic etching, one may sever substrate 105 from water 20 simply by cutting with a saw. In FIG. 25, cut lines 200, 202, 203 and 230 surround piezoelectric actuator 120 and define substrate 105. Substrate 105 may be given a sharp forward edge by angling the saw in cut 230 away from the horizontal.

A saw may be used to control the thickness of a horn. In such a process it is preferred to use a saw on substrate 60 which does not have piezoelectric actuator 120 attached. In FIGS. 26 and 27, a saw 240 with an axis of rotation parallel to the length of substrate 60 makes a series of cross-wise cuts into substrate 60. Where saw 240 makes contact with substrate 60, a portion of substrate 60 will be worn away. By controlling the depth to which saw 240 penetrates substrate 60, one may control the thickness of a particular length W of horn portion 64. Length W is equal to the width of saw 240, e.g., about 50 to 100 µm. By repeatedly cutting with saw 240 and then stepping substrate 60 forward by width W, one may make a series of cuts which grind away substrate 60 to form horn 64. If the width W of saw 240 is small, and the incremental change of depth of each step 243 is also small, a relatively smooth surface may be formed. Furthermore, by taking steps smaller than width W, one may exercise even finer control over the smoothness of the surface of horn 64.

In a typical manufacturing procedure, circular saw 240 would be attached to a robotic arm 245 which moves up and down. Substrate 60 would be solidly attached to a mount 246 which can move forward, back and cross-wise with respect to saw 240. Robotic arm 245 and mount 246 would be controlled by computer 247. The manufacturer would input the desired slope of horn 64 into computer 247 which would calculate the size of each step 243 taken by mount 246 and the depth to which saw 240 should cut in each step.

The incremental saw cut process may be used to create a variety of different horn shapes. For example, a horn may have a catenoidal (FIG. 28A), linear (FIG. 28B), or conical slope (FIG. 28C). In addition, saw 240 may cut either into the top surface of silicon substrate 60 (FIGS. 28A), the bottom surface of silicon substrate 60 (FIG. 28B) or both surfaces (FIG. 28C). One may even create a horn having a cascade shape (FIG. 28D). The length of each segment in a cascade-shaped horn would be one-quarter of a design wavelength. A cascade-shaped horn 64 may allow for very large displacement of forward edge 67 with only a small applied voltage due to the large amplification in a cascade-shaped horn. As shown in FIG. 27 a saw 260 may be used to control the width of horn 64 by orienting saw 260 to cut into front edge 67 of substrate 60. This would allow a manufacturer to create horns that vary in both thickness and width as a function of length.

A third process which may be used to control the shape of horn portion of the substrate is isotropic liquid etching. As shown in FIG. 29, in a liquid etching process, the substrate 60 is lowered into an acid bath 270. In this manufacturing procedure, silicon substrate 60 would be held by a grip 272 attached to a robotic arm 273 controlled by computer 275. The manufacturer may input a function into computer 275 which will control the depth of substrate 60 in the acid bath 270 as a function of time. In general, substrate 60 would be plunged into acid bath 270 and then slowly withdrawn. Because the acid dissolves the exposed portion of substrate 60 at a constant rate, the portion of substrate 60 which remains in acid bath 270 the longest will be the thinnest. As shown in FIG. 30, the resulting horn 64 would be evenly etched on all sides and tapered to a front edge 67. By controlling the speed with which substrate 60 is withdrawn from acid bath 270 by robotic arm 273, one may impart a catenoidal linear, conical, or other curve to horn 64.

The present invention has been described in terms of a number of embodiments. The invention, however, is not limited to the embodiments depicted and described. Rather, the scope of the invention is defined by the appended claims.

What is claimed is:

1. A surgical tool, comprising:

(a) a casing;

(b) a cutter formed of a first and a second microstructure bonded together, each of said microstructures having:

(i) a substrate of a first semiconducting material, said substrate having a body portion and a horn portion projecting forward from said body portion, (ii) said horn portion having a blade portion which is free to vibrate, said blade portion having a forward edge which is significantly thinner than said body portion, and said body portion having a top surface and a bottom surface, (iii) a piezoelectric actuator for imparting mechanical energy to said blade portion, said piezoelectric actuator mechanically coupled to the top surface of said body portion, and piezoelectric actuator including a first electrode layer, a second electrode layer, and a piezoelectric layer between said first and second electrode layers, and (iv) the bottom surfaces of the body portions of said first and second microstructures bonded together to form said cutter;

(c) means for mounting said cutter in said casing;

(d) means for supplying power to said first and second electrode layers; and (e) means for controlling said power supply means.

2. The tool of claim 1 wherein the respective bottom surfaces of the body portions of the first and second microstructures have a channel running lengthwise from the front to the back of said body portions, said first and second microstructures bonded so the channels are aligned to form a conduit for disposing of debris, said conduit running lengthwise from the front to the back of said cutter.

3. The tool of claim 2 further including a pump providing suction; and a tube inside said casing connecting the back end of said conduit to said pump to suck debris into said conduit.

* * * * *

UNITED STATES PATENT AND TRADEMARK OFFICE
CERTIFICATE OF CORRECTION

PATENT NO.      : 5,728,089

DATED           : 3/17/1998

INVENTOR(S)     : Lal et al.

It is certified that error appears in the above-identified patent and that said Letters Patent is hereby corrected as shown below:

Title page
OTHER PUBLICATIONS
add --Kalski, S., et al., "Vibrations and Waves," 1992, pp. 313-325--.

Signed and Sealed this

Eighteenth Day of May, 1999

Attest:

Q. TODD DICKINSON

Attesting Officer        Acting Commissioner of Patents and Trademarks